United States Patent
Chen et al.

(10) Patent No.: US 6,632,926 B1
(45) Date of Patent: Oct. 14, 2003

(54) ANTIBODY VARIANTS

(75) Inventors: Yvonne M. Chen, San Mateo, CA (US); Henry B. Lowman, El Granada, CA (US); Yves Muller, Zepernick (DE)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 09/440,781

(22) Filed: Nov. 16, 1999

Related U.S. Application Data

(60) Provisional application No. 60/108,945, filed on Nov. 18, 1998.

(51) Int. Cl.$^7$ .............................................. C07K 16/00
(52) U.S. Cl. ............................... 530/387.3; 530/388.85
(58) Field of Search .......................... 530/387.1, 387.3, 530/388.1, 388.22, 350, 388.8, 388.85; 424/130.1

(56) References Cited

U.S. PATENT DOCUMENTS

| | | | |
|---|---|---|---|
| 5,821,337 A | | 10/1998 | Carter et al. |
| 6,010,861 A | * | 1/2000 | Blume |
| 6,037,454 A | * | 3/2000 | Jardieu et al. |

FOREIGN PATENT DOCUMENTS

| | | |
|---|---|---|
| CA | 2125240 | 12/1995 |
| JP | 91-40386 | 6/1997 |
| WO | WO 97/31024 | 8/1997 |
| WO | WO 98/23746 | 6/1998 |
| WO | WO 98/23761 | 6/1998 |
| WO | WO 98/45331 | 10/1998 |
| WO | WO 98/45332 | 10/1998 |

OTHER PUBLICATIONS

Groves et al., hybridoma 6:71–76, 1987.*
Jones et al., Nature 321:522–525, 1986.*
Panka et al., Proc. Natl. Acad. Sci. USA 85:3080–3084, 1988.*
Rudikoff et al Proc. Natl. Acad. Sci. USA 79:1979, 1982.*
Amit et al., Science 233:747–753, 1986.*
Simon et al., Protein Engineering 5:229–234, 1992.*
Balint and Larrick, "Antibody engineering by parsimonious mutagenesis" *Gene* 137 (1) :109–118 (Dec. 27, 1993).
Barbas III et al., "In vitro evolution of a neutralizing human antibody to human immunodeficiency virus type 1 to enhance affinity and broaden strain cross–reactivity" *Proc. Natl. Acad. Sci. USA* 91(9) :3809–3813 (Apr. 26, 1994).
Brunger et al., "Crystallographic R factor refinement by molecular dynamics" *Science* 235:458–460 (Jan. 23, 1987).
Chiswell and McCafferty, "Phage antibodies: will new 'coliclonal' antibodies replace monoclonal antibodies?" *Trends In Biotechnology* 10(3) :80–84 (Mar. 1992).
Gazzano–Santoro et al., "A non–radioactive complement–dependent cytotoxicity assay for anti–CD20 monoclonal antibody" *Journal of Immunological Methods* 202:163–171 (1997).
Hawkins et al., "Selection of Phage Antibodies by Binding Affinity Mimicking Affinity Maturation" *J. Mol. Biol.* 226:889–896 (1992).
LeBlanc et al., "Recognition properties of a sequence–specific DNA binding antibody" *Biochemistry* 37(17) : 6015–6022 (Apr. 28, 1998).

Lee et al., "Strong inhibition of fibrinogen binding to platelet receptor $^\alpha IIb^{\beta 3}$ by RGD sequences installed into a presentation scaffold" *Protein Engineering* 6 (7) :745–754 (Sep. 1993).
McLane et al., "Transplantation of a 17–amino acid α–helical DNA–binding domain into an antibody molecule confers sequence–dependent DNA recognition" *Proc. Natl. Acad. Sci. USA* 92 (11) :5214–5218 (May 23, 1995).
Muller et al., "VEGF and the Fab fragment of a humanized neutralizing antibody: crystal structure of the complex at 2.4 A resolution and mutational analysis of the interface" *Structure* 6(9) :1153–1167 (Sep. 15, 1998).
Presta et al., "Humanization of an Anti–Vascular Endothelial Growth Factor Monoclonal Antibody for the Therapy of Solid Tumors and Other Disorders" *Cancer Research* 57 (20) :4593–4599 (Oct. 15, 1997).
Rader and Barbas III, "Phage display of combinatorial antibody libraries" *Current Opinion in Biotechnology* 8 (4) : 503–508 (Aug. 1997).
Schier et al., "Isolation of picomolar affinity anti–c–erbB–2 single–chain Fv by molecular evolution of the complementarity determining regions in the center of the antibody binding site" *Journal of Molecular Biology* 263 (4) : 551–567 (Nov. 8, 1996).
Sheets et al., "Efficient construction of a large nonimmune phage antibody library: the production of high–affinity human single–chain antibodies to protein antigens" *Proc. Natl. Acad. Sci. USA* 95(11) :6157–6162 (May 26, 1998).
Thompson et al., "Affinity maturation of a high–affinity monoclonal antibody against the third hypervariable loop of human immunodeficiency virus: use of phage display to improve affinity and broaden strain reactivity" *Journal of Molecular Biology* 256 (1) :77–78 (Feb. 16, 1996).
Wu et al., "Stepwise in vitro affinity maturation of Vitaxin, an $\alpha_v\beta_3$–specific humanized mAb" *Proc. Natl. Acad. Sci. USA* 95 (11) :6037–6042 (May 26, 1998).
Yang et al., "CDR walking mutagenesis for the affinity maturation of a potent human anti–HIV–1 antibody into the picomolar range" *Journal of Molecular Biology* 254(3) : 392–403 (Dec. 1, 1995).
Zhao et al., "A paradigm for drug discovery using a conformation from the crystal structure of a presentation scaffold" *Nature Structural Biology* 2(12) :1131–1137 (Dec. 1995).
Fenney and Thuerauf, "Sequence and fine specificity analysis of primary 511 anti–phosphorylcholine antibodies" *Journal of Immunology* 143 (12) :4061–4068 (Dec. 15, 1989).
Ohlin and Borrebaeck, "Insertions and deletions in hypervariable loops of antibody heavy chains contribute to molecular diversity" *Molecular Immunology* 35 (4) : 233–238 (Mar. 1998).
Wilson et al., "Somatic hypermutation introduces insertions and deletions into immunoglobulin V genes" *Journal of Experimental Medicine* 187 (1) :59–70 (Jan. 5, 1998).

* cited by examiner

*Primary Examiner*—Sheela Huff
*Assistant Examiner*—Larry Helms
(74) *Attorney, Agent, or Firm*—Steven X. Cui

(57) ABSTRACT

Antibody variants of parent antibodies are disclosed which have one or more amino acids inserted in a hypervariable region of the parent antibody and a binding affinity for a target antigen which is at least about two fold stronger than the binding affinity of the parent antibody for the antigen.

3 Claims, 6 Drawing Sheets

☐ = differences from F(ab)-12

```
                 10                  20                  30
F(ab)-12   DIQMTQSPSSLSASVGDRVTITCSASQDISNYLNWYQQ
Y0192      DIQLTQSPSSLSASVGDRVTITCRANEQLSNYLNWYQQ
Y0238-3    DIQLTQSPSSLSASVGDRVTITCRANEQLSNYLNWYQQ
Y0239-19   DIQLTQSPSSLSASVGDRVTITCRANEQLSNYLNWYQQ
Y0313-2    DIQLTQSPSSLSASVGDRVTITCRANEQLSNYLNWYQQ
                                           CDR-L1
                 40        50        60        70
F(ab)-12   KPGKAPKVLIYFTSSLHSGVPSRFSGSGSGTDFTLTIS
Y0192      KPGKAPKVLIYFTSSLHSGVPSRFSGSGSGTDFTLTIS
Y0238-3    KPGKAPKVLIYFTSSLHSGVPSRFSGSGSGTDFTLTIS
Y0239-19   KPGKAPKVLIYFTSSLHSGVPSRFSGSGSGTDFTLTIS
Y0313-2    KPGKAPKVLIYFTSSLHSGVPSRFSGSGSGTDFTLTIS
                   CDR-L2
                 80        90       100
F(ab)-12   SLQPEDFATYYCQQYSTVPWTFGQGTKVEIKRTV  (SEQ ID NO:94)
Y0192      SLQPEDFATYYCQQYSTVPWTFGQGTKVEIKRTV  (SEQ ID NO:95)
Y0238-3    SLQPEDFATYYCQQYSTVPWTFGQGTKVEIKRTV  (SEQ ID NO:95)
Y0239-19   SLQPEDFATYYCQQYSTVPWTFGQGTKVEIKRTV  (SEQ ID NO:95)
Y0313-2    SLQPEDFATYYCQQYSTVPWTFGQGTKVEIKRTV  (SEQ ID NO:95)
                         CDR-L3
```

FIG._1A

☐ = differences from F(ab)-12

```
              10         20         30
F(ab)-12  EVQLVESGGGLVQPGGSLRLSCAASGYTFTNYGMNWVR
Y0192     EVQLVESGGGLVQPGGSLRLSCAASGYTFTNYGMNWVR
Y0238-3   EVQLVESGGGLVQPGGSLRLSCAASGYDFTHYGMNWVR
Y0239-19  EVQLVESGGGLVQPGGSLRLSCAASGYTFTNYGMNWVR
Y0313-2   EVQLVESGGGLVQPGGSLRLSCAASGYDFTHYGMNWVR
                                    ─────────
                                      CDR-H1

40         50         60         70
F(ab)-12  QAPGKGLEWVGWINTYTGEPTYAADFKRRFTFSLDTSKSTA
Y0192     QAPGKGLEWVGWINTYTGEPTYAADFKRRFTFSLDTSKSTA
Y0238-3   QAPGKGLEWVGWINTYTGEPTYAADFKRRFTFSLDTSKSTA
Y0239-19  QAPGKGLEWVGWINTYTGEPTYAADFKRRFTFSLDTSKSTA
Y0313-2   QAPGKGLEWVGWINTYTGEPTYAADFKRRFTFSLDTSKSTA
                      ───────────────
                           CDR-H2

80         90        100
F(ab)-12  YLQMNSLRAEDTAVYYCAKYPHYYG---SSHWYFDVWGQGTL   (SEQ ID NO:96)
Y0192     YLQMNSLRAEDTAVYYCAKYPHYYG---SSHWYFDVWGQGTL   (SEQ ID NO:96)
Y0238-3   YLQMNSLRAEDTAVYYCAKYPHYYG---SSHWYFDVWGQGTL   (SEQ ID NO:97)
Y0239-19  YLQMNSLRAEDTAVYYCAKYPHYVNERKSHWYFDVWGQGTL    (SEQ ID NO:98)
Y0313-2   YLQMNSLRAEDTAVYYCAKYPHYVNERKSHWYFDVWGQGTL    (SEQ ID NO:99)
                                  ──── ─────────
                                  CDR-7
                                       CDR-H3
```

FIG._1B

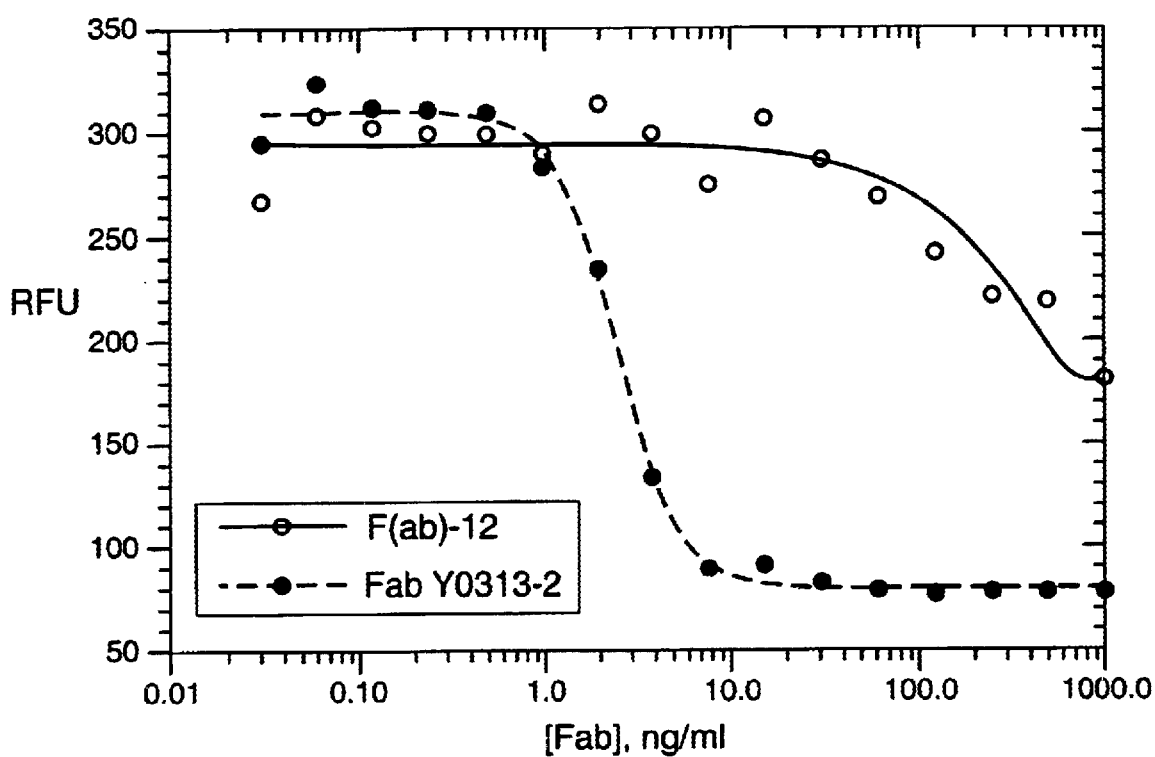
FIG._2

SEQUENCE LISTING

```
<160> NUMBER OF SEQ ID NOS: 99

<210> SEQ ID NO 1
<211> LENGTH: 32
<212> TYPE: DNA
<213> ORGANISM: artificial sequence
<220> FEATURE:
<221> NAME/KEY: artificial
```

```
<222> LOCATION: 1-32
<223> OTHER INFORMATION: frameshift oligo

<400> SEQUENCE: 1
ctgtcaacag tatagctacc gtgccgtgga cg                              32

<210> SEQ ID NO 2
<211> LENGTH: 32
<212> TYPE: DNA
<213> ORGANISM: artificial sequence
<220> FEATURE:
<221> NAME/KEY: artificial
<222> LOCATION: 1-32
<223> OTHER INFORMATION: frameshift oligo

<400> SEQUENCE: 2
gcagcttctg gctatgacct tcaccaacta tg                              32

<210> SEQ ID NO 3
<211> LENGTH: 33
<212> TYPE: DNA
<213> ORGANISM: artificial sequence
<220> FEATURE:
<221> NAME/KEY: artificial
<222> LOCATION: 1-33
<223> OTHER INFORMATION: frameshift oligo

<400> SEQUENCE: 3
gatggattaa cacctatgac cggtgaaccg acc                             33

<210> SEQ ID NO 4
<211> LENGTH: 34
<212> TYPE: DNA
<213> ORGANISM: artificial sequence
<220> FEATURE:
<221> NAME/KEY: artificial
<222> LOCATION: 1-34
<223> OTHER INFORMATION: frameshift oligo

<400> SEQUENCE: 4
gatggattaa cacctattga accgacctat gctg                            34

<210> SEQ ID NO 5
<211> LENGTH: 35
<212> TYPE: DNA
<213> ORGANISM: artificial sequence
<220> FEATURE:
<221> NAME/KEY: artificial
<222> LOCATION: 1-35
<223> OTHER INFORMATION: frameshift oligo

<400> SEQUENCE: 5
gtacccgcac tattatgagc agccactggt atttc                           35

<210> SEQ ID NO 6
<211> LENGTH: 32
<212> TYPE: DNA
<213> ORGANISM: artificial sequence
<220> FEATURE:
<221> NAME/KEY: artificial
<222> LOCATION: 1-32
<223> OTHER INFORMATION: frameshift oligo

<400> SEQUENCE: 6
gtacccgcac tattatgagc cactggtatt tc                              32

<210> SEQ ID NO 7
```

<211> LENGTH: 43
<212> TYPE: DNA
<213> ORGANISM: artificial sequence
<220> FEATURE:
<221> NAME/KEY: artificial
<222> LOCATION: 1-43
<223> OTHER INFORMATION: random oligo
<220> FEATURE:
<221> NAME/KEY: unknown
<222> LOCATION: 17-18, 20-21, 23-24, 26-27
<223> OTHER INFORMATION: unknown base

<400> SEQUENCE: 7
ctgtcaacag tatagcnnsn nsnnsnnsac cgtgccgtgg acg        43

<210> SEQ ID NO 8
<211> LENGTH: 49
<212> TYPE: DNA
<213> ORGANISM: artificial sequence
<220> FEATURE:
<221> NAME/KEY: artificial
<222> LOCATION: 1-49
<223> OTHER INFORMATION: random oligo
<220> FEATURE:
<221> NAME/KEY: unknown
<222> LOCATION: 17-18, 20-21, 23-24, 26-27, 29-30, 32-33
<223> OTHER INFORMATION: unknown base

<400> SEQUENCE: 8
ctgtcaacag tatagcnnsn nsnnsnnsnn snnsaccgtg ccgtggacg        49

<210> SEQ ID NO 9
<211> LENGTH: 43
<212> TYPE: DNA
<213> ORGANISM: artificial sequence
<220> FEATURE:
<221> NAME/KEY: artificial
<222> LOCATION: 1-43
<223> OTHER INFORMATION: random oligo
<220> FEATURE:
<221> NAME/KEY: unknown
<222> LOCATION: 16-17, 19-20, 22-23, 25-26
<223> OTHER INFORMATION: unknown base

<400> SEQUENCE: 9
gcagcttctg gctatnnsnn snnsnnsacc ttcaccaact atg        43

<210> SEQ ID NO 10
<211> LENGTH: 46
<212> TYPE: DNA
<213> ORGANISM: artificial sequence
<220> FEATURE:
<221> NAME/KEY: artificial
<222> LOCATION: 1-46
<223> OTHER INFORMATION: random oligo
<220> FEATURE:
<221> NAME/KEY: unknown
<222> LOCATION: 16-17, 19-20, 22-23, 25-26, 28-29
<223> OTHER INFORMATION: unknown base

<400> SEQUENCE: 10
gcagcttctg gctatnnsnn snnsnnsnns accttcacca actatg        46

<210> SEQ ID NO 11
<211> LENGTH: 49
<212> TYPE: DNA
<213> ORGANISM: artificial sequence
<220> FEATURE:
<221> NAME/KEY: artificial
<222> LOCATION: 1-49
<223> OTHER INFORMATION: random oligo

```
<220> FEATURE:
<221> NAME/KEY: unknown
<222> LOCATION: 16-17, 19-20, 22-23, 25-26, 28-29, 31-32
<223> OTHER INFORMATION: unknown base

<400> SEQUENCE: 11
gcagcttctg gctatnnsnn snnsnnsnns nnsaccttca ccaactatg            49

<210> SEQ ID NO 12
<211> LENGTH: 41
<212> TYPE: DNA
<213> ORGANISM: artificial sequence
<220> FEATURE:
<221> NAME/KEY: artificial
<222> LOCATION: 1-41
<223> OTHER INFORMATION: random oligo
<220> FEATURE:
<221> NAME/KEY: unknown
<222> LOCATION: 18-19, 21-22, 24-25
<223> OTHER INFORMATION: unknown base

<400> SEQUENCE: 12
gatggattaa cacctatnns nnsnnsaccg gtgaaccgac c                    41

<210> SEQ ID NO 13
<211> LENGTH: 44
<212> TYPE: DNA
<213> ORGANISM: artificial sequence
<220> FEATURE:
<221> NAME/KEY: artificial
<222> LOCATION: 1-44
<223> OTHER INFORMATION: random oligo
<220> FEATURE:
<221> NAME/KEY: unknown
<222> LOCATION: 18-19, 21-22, 24-25, 27-28
<223> OTHER INFORMATION: unknown base

<400> SEQUENCE: 13
gatggattaa cacctatnns nnsnnsnnsa ccggtgaacc gacc                 44

<210> SEQ ID NO 14
<211> LENGTH: 51
<212> TYPE: DNA
<213> ORGANISM: artificial sequence
<220> FEATURE:
<221> NAME/KEY: artificial
<222> LOCATION: 1-51
<223> OTHER INFORMATION: random oligo
<220> FEATURE:
<221> NAME/KEY: unknown
<222> LOCATION: 18-19, 21-22, 24-25, 27-28, 30-31, 33-34
<223> OTHER INFORMATION: unknown base

<400> SEQUENCE: 14
gatggattaa cacctatnns nnsnnsnnsn nsnnsgaacc gacctatgct           50
g                                                                51

<210> SEQ ID NO 15
<211> LENGTH: 46
<212> TYPE: DNA
<213> ORGANISM: artificial sequence
<220> FEATURE:
<221> NAME/KEY: artificial
<222> LOCATION: 1-46
<223> OTHER INFORMATION: random oligo
<220> FEATURE:
<221> NAME/KEY: unknown
<222> LOCATION: 17-18, 20-21, 23-24, 26-27
<223> OTHER INFORMATION: unknown base
```

```
<400> SEQUENCE: 15
gtacccgcac tattatnnsn nsnnsnnsag cagccactgg tatttc                    46

<210> SEQ ID NO 16
<211> LENGTH: 46
<212> TYPE: DNA
<213> ORGANISM: artificial sequence
<220> FEATURE:
<221> NAME/KEY: artificial
<222> LOCATION: 1-46
<223> OTHER INFORMATION: random oligo
<220> FEATURE:
<221> NAME/KEY: unknown
<222> LOCATION: 17-18, 20-21, 23-24, 26-27
<223> OTHER INFORMATION: unknown base

<400> SEQUENCE: 16
gtacccgcac tattatnnsn nsnnsnnsag cagccactgg tatttc                    46

<210> SEQ ID NO 17
<211> LENGTH: 46
<212> TYPE: DNA
<213> ORGANISM: artificial sequence
<220> FEATURE:
<221> NAME/KEY: artificial
<222> LOCATION: 1-46
<223> OTHER INFORMATION: random oligo
<220> FEATURE:
<221> NAME/KEY: unknown
<222> LOCATION: 17-18, 20-21, 23-24, 26-27, 29-30
<223> OTHER INFORMATION: unknown base

<400> SEQUENCE: 17
gtacccgcac tattatnnsn nsnnsnnsnn sagccactgg tatttc                    46

<210> SEQ ID NO 18
<211> LENGTH: 49
<212> TYPE: DNA
<213> ORGANISM: artificial sequence
<220> FEATURE:
<221> NAME/KEY: artificial
<222> LOCATION: 1-49
<223> OTHER INFORMATION: random oligo
<220> FEATURE:
<221> NAME/KEY: unknown
<222> LOCATION: 17-18, 20-21, 23-24, 26-27, 29-30, 32-33
<223> OTHER INFORMATION: unknown base

<400> SEQUENCE: 18
gtacccgcac tattatnnsn nsnnsnnsnn snnsagccac tggtatttc                 49

<210> SEQ ID NO 19
<211> LENGTH: 10
<212> TYPE: PRT
<213> ORGANISM: artificial sequence
<220> FEATURE:
<221> NAME/KEY: artificial
<222> LOCATION: 1-10
<223> OTHER INFORMATION: variant CDR sequence

<400> SEQUENCE: 19

Gly Tyr Asp Phe Thr Asn Tyr Gly Ile Asn
 1               5                  10

<210> SEQ ID NO 20
<211> LENGTH: 10
<212> TYPE: PRT
<213> ORGANISM: artificial sequence
<220> FEATURE:
```

```
<221> NAME/KEY: artificial
<222> LOCATION: 1-10
<223> OTHER INFORMATION: variant CDR sequence

<400> SEQUENCE: 20

Gly Tyr Asp Tyr Thr Asn Tyr Gly Ile Asn
 1               5                  10

<210> SEQ ID NO 21
<211> LENGTH: 10
<212> TYPE: PRT
<213> ORGANISM: artificial sequence
<220> FEATURE:
<221> NAME/KEY: artificial
<222> LOCATION: 1-10
<223> OTHER INFORMATION: variant CDR sequence

<400> SEQUENCE: 21

Gly Tyr Asp Trp Thr Asn Tyr Gly Ile Asn
 1               5                  10

<210> SEQ ID NO 22
<211> LENGTH: 13
<212> TYPE: PRT
<213> ORGANISM: artificial sequence
<220> FEATURE:
<221> NAME/KEY: artificial
<222> LOCATION: 1-13
<223> OTHER INFORMATION: variant CDR sequence

<400> SEQUENCE: 22

Trp Ile Asn Thr Trp Thr Gly Glu Pro Thr Tyr Ala Ala
 1               5                  10          13

<210> SEQ ID NO 23
<211> LENGTH: 9
<212> TYPE: PRT
<213> ORGANISM: artificial sequence
<220> FEATURE:
<221> NAME/KEY: artificial
<222> LOCATION: 1-9
<223> OTHER INFORMATION: variant CDR sequence

<400> SEQUENCE: 23

Gln Gln Tyr Ser Ala Thr Pro Trp Thr
 1               5               9

<210> SEQ ID NO 24
<211> LENGTH: 9
<212> TYPE: PRT
<213> ORGANISM: artificial sequence
<220> FEATURE:
<221> NAME/KEY: artificial
<222> LOCATION: 1-9
<223> OTHER INFORMATION: variant CDR sequence

<400> SEQUENCE: 24

Gln Gln Tyr Ser Asn Val Pro Trp Thr
 1               5               9

<210> SEQ ID NO 25
<211> LENGTH: 9
<212> TYPE: PRT
<213> ORGANISM: artificial sequence
<220> FEATURE:
<221> NAME/KEY: artificial
<222> LOCATION: 1-9
<223> OTHER INFORMATION: variant CDR sequence
```

```
<400> SEQUENCE: 25

Gln Gln Tyr Ser Ala Val Pro Trp Thr
 1               5                   9

<210> SEQ ID NO 26
<211> LENGTH: 9
<212> TYPE: PRT
<213> ORGANISM: artificial sequence
<220> FEATURE:
<221> NAME/KEY: artificial
<222> LOCATION: 1-9
<223> OTHER INFORMATION: variant CDR sequence

<400> SEQUENCE: 26

Gln Gln Tyr Ser Ser Val Pro Trp Thr
 1               5                   9

<210> SEQ ID NO 27
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 27

Tyr Pro His Tyr Tyr Ala Lys Glu Arg Ser Ser His Trp Tyr Phe
 1               5                   10                  15

Asp Val
     17

<210> SEQ ID NO 28
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 28

Tyr Pro His Tyr Tyr Val Gly Glu Thr Ser Ser His Trp Tyr Phe
 1               5                   10                  15

Asp Val
     17

<210> SEQ ID NO 29
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 29

Tyr Pro His Tyr Tyr Ala Arg Asp Arg Ser Ser His Trp Tyr Phe
 1               5                   10                  15

Asp Val
     17

<210> SEQ ID NO 30
<211> LENGTH: 18
<212> TYPE: PRT
<213> ORGANISM: artificial sequence
```

```
<220> FEATURE:
<221> NAME/KEY: artificial
<222> LOCATION: 1-18
<223> OTHER INFORMATION: variant CDR sequence

<400> SEQUENCE: 30

Tyr Pro His Tyr Tyr Glu Arg Asp Gly Lys Ser Ser His Trp Tyr
 1               5                   10                  15
Phe Asp Val
        18

<210> SEQ ID NO 31
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 31

Tyr Pro His Tyr Tyr Arg Asn Glu Lys Ser Ser His Trp Tyr Phe
 1               5                   10                  15
Asp Val
     17

<210> SEQ ID NO 32
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 32

Tyr Pro His Tyr Tyr Val Gly Glu Gln Ser Ser His Trp Tyr Phe
 1               5                   10                  15
Asp Val
     17

<210> SEQ ID NO 33
<211> LENGTH: 17
<212> TYPE: PRT
<213> ORGANISM: artificial sequece
<220> FEATURE:
<221> NAME/KEY: artificial
<222> LOCATION: 1-17
<223> OTHER INFORMATION: variant CDR sequence

<400> SEQUENCE: 33

Tyr Pro His Tyr Tyr Gln Arg Asp Arg Ser Ser His Trp Tyr Phe
 1               5                   10                  15
Asp Val
     17

<210> SEQ ID NO 34
<211> LENGTH: 18
<212> TYPE: PRT
<213> ORGANISM: artificial sequence
<220> FEATURE:
<221> NAME/KEY: artificial
<222> LOCATION: 1-18
<223> OTHER INFORMATION: variant CDR sequence

<400> SEQUENCE: 34
```

Tyr Pro His Tyr Tyr Gln Lys Gln Ser Lys Ser Ser His Trp Tyr
 1               5                  10                  15

Phe Asp Val
        18

<210> SEQ ID NO 35
<211> LENGTH: 18
<212> TYPE: PRT
<213> ORGANISM: artificial sequence
<220> FEATURE:
<221> NAME/KEY: artificial
<222> LOCATION: 1-18
<223> OTHER INFORMATION: variant CDR sequence

<400> SEQUENCE: 35

Tyr Pro His Tyr Tyr Gln Asn Glu Gly Pro Ser Ser His Trp Tyr
 1               5                  10                  15

Phe Asp Val
        18

<210> SEQ ID NO 36
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 36

Tyr Pro His Tyr Tyr Gly Asn His Arg Ser Ser His Trp Tyr Phe
 1               5                  10                  15

Asp Val
    17

<210> SEQ ID NO 37
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 37

Tyr Pro His Tyr Tyr Arg Thr Glu Lys Ser Ser His Trp Tyr Phe
 1               5                  10                  15

Asp Val
    17

<210> SEQ ID NO 38
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 38

Tyr Pro His Tyr Tyr Leu Lys Asp Arg Ser Ser His Trp Tyr Phe
 1               5                  10                  15

Asp Val
    17

```
<210> SEQ ID NO 39
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 39

Tyr Pro His Tyr Tyr Gln Asp Glu Lys Ser Ser His Trp Tyr Phe
 1               5                  10                  15
Asp Val
      17

<210> SEQ ID NO 40
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 40

Tyr Pro His Tyr Tyr Val Gly Glu Lys Ser Ser His Trp Tyr Phe
 1               5                  10                  15
Asp Val
      17

<210> SEQ ID NO 41
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 41

Tyr Pro His Tyr Tyr Arg Asp Glu Arg Ser Ser His Trp Tyr Phe
 1               5                  10                  15
Asp Val
      17

<210> SEQ ID NO 42
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 42

Tyr Pro His Tyr Tyr Thr Tyr Asp Lys Ser Ser His Trp Tyr Phe
 1               5                  10                  15
Asp Val
      17

<210> SEQ ID NO 43
<211> LENGTH: 18
<212> TYPE: PRT
<213> ORGANISM: artificial sequence
<220> FEATURE:
<221> NAME/KEY: artificial
<222> LOCATION: 1-18
```

```
<223> OTHER INFORMATION: variant CDR sequence

<400> SEQUENCE: 43

Tyr Pro His Tyr Tyr His Thr Arg Gly Gly Ser Ser His Trp Tyr
 1               5                  10                  15

Phe Asp Val
        18

<210> SEQ ID NO 44
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 44

Tyr Pro His Tyr Tyr Leu Asn Asp Lys Ser Ser His Trp Tyr Phe
 1               5                  10                  15

Asp Val
    17

<210> SEQ ID NO 45
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 45

Tyr Pro His Tyr Tyr Tyr Arg Asp Arg Ser Ser His Trp Tyr Phe
 1               5                  10                  15

Asp Val
    17

<210> SEQ ID NO 46
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 46

Tyr Pro His Tyr Tyr Arg Asn Glu Arg Ser Ser His Trp Tyr Phe
 1               5                  10                  15

Asp Val
    17

<210> SEQ ID NO 47
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 47

Tyr Pro His Tyr Tyr Lys Asn Asp Lys Ser Ser His Trp Tyr Phe
 1               5                  10                  15
```

Asp Val
    17

<210> SEQ ID NO 48
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 48

Tyr Pro His Tyr Tyr Leu Ala Asp Arg Ser Ser His Trp Tyr Phe
 1               5                  10                  15

Asp Val
    17

<210> SEQ ID NO 49
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 49

Tyr Pro His Tyr Tyr Val Asn Glu Arg Ser Ser His Trp Tyr Phe
 1               5                  10                  15

Asp Val
    17

<210> SEQ ID NO 50
<211> LENGTH: 17
<212> TYPE: PRT
<213> ORGANISM: artifical sequence
<220> FEATURE:
<221> NAME/KEY: artificial
<222> LOCATION: 1-17
<223> OTHER INFORMATION: variant CDR sequence

<400> SEQUENCE: 50

Tyr Pro His Tyr Tyr Leu Lys Asp Lys Ser Ser His Trp Tyr Phe
 1               5                  10                  15

Asp Val
    17

<210> SEQ ID NO 51
<211> LENGTH: 18
<212> TYPE: PRT
<213> ORGANISM: artificial sequence
<220> FEATURE:
<221> NAME/KEY: artificial
<222> LOCATION: 1-18
<223> OTHER INFORMATION: variant CDR sequence

<400> SEQUENCE: 51

Tyr Pro His Tyr Tyr Leu Lys Asp Gly Arg Ser Ser His Trp Tyr
 1               5                  10                  15

Phe Asp Val
        18

<210> SEQ ID NO 52
<211> LENGTH: 18
<212> TYPE: PRT

```
<213> ORGANISM: artificial sequence
<220> FEATURE:
<221> NAME/KEY: artificial
<222> LOCATION: 1-18
<223> OTHER INFORMATION: variant CDR sequence

<400> SEQUENCE: 52

Tyr Pro His Tyr Tyr Glu Arg Asp Gly Arg Ser Ser His Trp Tyr
 1               5                  10                  15

Phe Asp Val
        18

<210> SEQ ID NO 53
<211> LENGTH: 18
<212> TYPE: PRT
<213> ORGANISM: artificial sequence
<220> FEATURE:
<221> NAME/KEY: artificial
<222> LOCATION: 1-18
<223> OTHER INFORMATION: variant CDR sequence

<400> SEQUENCE: 53

Tyr Pro His Tyr Tyr Leu Arg Asp Gly Arg Ser Ser His Trp Tyr
 1               5                  10                  15

Phe Asp Val
        18

<210> SEQ ID NO 54
<211> LENGTH: 16
<212> TYPE: PRT
<213> ORGANISM: artificial sequence
<220> FEATURE:
<221> NAME/KEY: artificial
<222> LOCATION: 1-16
<223> OTHER INFORMATION: variant CDR sequence

<400> SEQUENCE: 54

Tyr Pro His Tyr Tyr Leu Gly Glu Ser Ser His Trp Tyr Phe Asp
 1               5                  10                  15

Val
 16

<210> SEQ ID NO 55
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 55

Tyr Pro His Tyr Tyr Leu Gly Glu Lys Ser Ser His Trp Tyr Phe
 1               5                  10                  15

Asp Val
    17

<210> SEQ ID NO 56
<211> LENGTH: 18
<212> TYPE: PRT
<213> ORGANISM: artificial sequence
<220> FEATURE:
<221> NAME/KEY: artificial
<222> LOCATION: 1-18
<223> OTHER INFORMATION: variant CDR sequence

<400> SEQUENCE: 56
```

Tyr Pro His Tyr Tyr Leu Lys Asp Arg Arg Ser Ser His Trp Tyr
 1               5                  10                  15

Phe Asp Val
        18

<210> SEQ ID NO 57
<211> LENGTH: 18
<212> TYPE: PRT
<213> ORGANISM: artificial sequence
<220> FEATURE:
<221> NAME/KEY: artificial
<222> LOCATION: 1-18
<223> OTHER INFORMATION: variant CDR sequence

<400> SEQUENCE: 57

Tyr Pro His Tyr Tyr Leu Lys Asp Gly Met Ser Ser His Trp Tyr
 1               5                  10                  15

Phe Asp Val
        18

<210> SEQ ID NO 58
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 58

Tyr Pro His Tyr Tyr Glu Lys Gln Arg Lys Ser His Trp Tyr Phe
 1               5                  10                  15

Asp Val
    17

<210> SEQ ID NO 59
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 59

Tyr Pro His Tyr Tyr Lys Glu Asp Lys Lys Ser His Trp Tyr Phe
 1               5                  10                  15

Asp Val
    17

<210> SEQ ID NO 60
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 60

Tyr Pro His Tyr Tyr Ser His Gln Lys Arg Ser His Trp Tyr Phe
 1               5                  10                  15

Asp Val
    17

```
<210> SEQ ID NO 61
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 61

Tyr Pro His Tyr Tyr Ser Gly Glu Arg Glu Ser His Trp Tyr Phe
  1               5                  10                  15
Asp Val
     17

<210> SEQ ID NO 62
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 62

Tyr Pro His Tyr Tyr Gln Ser Glu Gly Arg Ser His Trp Tyr Phe
  1               5                  10                  15
Asp Val
     17

<210> SEQ ID NO 63
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 63

Tyr Pro His Tyr Tyr Ser Val Glu Gly Gly Ser His Trp Tyr Phe
  1               5                  10                  15
Asp Val
     17

<210> SEQ ID NO 64
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 64

Tyr Pro His Tyr Tyr Pro Ser Pro Arg Gly Ser His Trp Tyr Phe
  1               5                  10                  15
Asp Val
     17

<210> SEQ ID NO 65
<211> LENGTH: 17
<212> TYPE: PRT
<213> ORGANISM: artificial sequence
<220> FEATURE:
<221> NAME/KEY: artificial
```

```
<222> LOCATION: 1-17
<223> OTHER INFORMATION: variant CDR sequence

<400> SEQUENCE: 65

Tyr Pro His Tyr Tyr Gln Arg Asn Gly Lys Ser His Trp Tyr Phe
 1               5                  10                  15

Asp Val
     17

<210> SEQ ID NO 66
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 66

Tyr Pro His Tyr Tyr Ala Arg Glu Gly Gly Ser His Trp Tyr Phe
 1               5                  10                  15

Asp Val
     17

<210> SEQ ID NO 67
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 67

Tyr Pro His Tyr Tyr Ser Asn Glu Arg Lys Ser His Trp Tyr Phe
 1               5                  10                  15

Asp Val
     17

<210> SEQ ID NO 68
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 68

Tyr Pro His Tyr Tyr Arg Gly Asp Arg Lys Ser His Trp Tyr Phe
 1               5                  10                  15

Asp Val
     17

<210> SEQ ID NO 69
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 69

Tyr Pro His Tyr Tyr Ser Asp Glu Lys Lys Ser His Trp Tyr Phe
 1               5                  10                  15
```

Asp Val
    17

<210> SEQ ID NO 70
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 70

Tyr Pro His Tyr Tyr Arg Ser Gln Arg Lys Ser His Trp Tyr Phe
 1               5                  10                  15

Asp Val
    17

<210> SEQ ID NO 71
<211> LENGTH: 18
<212> TYPE: PRT
<213> ORGANISM: artificial sequence
<220> FEATURE:
<221> NAME/KEY: artificial
<222> LOCATION: 1-18
<223> OTHER INFORMATION: variant CDR sequence

<400> SEQUENCE: 71

Tyr Pro His Tyr Tyr Ala Trp Arg Asp Arg Arg Ser His Trp Tyr
 1               5                  10                  15

Phe Asp Val
        18

<210> SEQ ID NO 72
<211> LENGTH: 18
<212> TYPE: PRT
<213> ORGANISM: artificial sequence
<220> FEATURE:
<221> NAME/KEY: artificial
<222> LOCATION: 1-18
<223> OTHER INFORMATION: variant CDR sequence

<400> SEQUENCE: 72

Tyr Pro His Tyr Tyr Ala Asn Arg Glu Arg Lys Ser His Trp Tyr
 1               5                  10                  15

Phe Asp Val
        18

<210> SEQ ID NO 73
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 73

Tyr Pro His Tyr Tyr Val Asn Asp Lys Thr Ser His Trp Tyr Phe
 1               5                  10                  15

Asp Val
    17

<210> SEQ ID NO 74
<211> LENGTH: 17

```
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 74

Tyr Pro His Tyr Tyr Val Glu Glu Thr Glu Ser His Trp Tyr Phe
  1               5                  10                  15

Asp Val
     17

<210> SEQ ID NO 75
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 75

Tyr Pro His Tyr Tyr Glu Lys Glu Arg Lys Ser His Trp Tyr Phe
  1               5                  10                  15

Asp Val
     17

<210> SEQ ID NO 76
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 76

Tyr Pro His Tyr Tyr Ser His Glu Arg Val Ser His Trp Tyr Phe
  1               5                  10                  15

Asp Val
     17

<210> SEQ ID NO 77
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 77

Tyr Pro His Tyr Tyr Arg Asp Glu Arg Glu Ser His Trp Tyr Phe
  1               5                  10                  15

Asp Val
     17

<210> SEQ ID NO 78
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence
```

```
<400> SEQUENCE: 78

Tyr Pro His Tyr Tyr Ala His Glu Lys Lys Ser His Trp Tyr Phe
 1               5                  10                  15
Asp Val
     17

<210> SEQ ID NO 79
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 79

Tyr Pro His Tyr Tyr Leu Lys Asp Arg Lys Ser His Trp Tyr Phe
 1               5                  10                  15
Asp Val
     17

<210> SEQ ID NO 80
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 80

Tyr Pro His Tyr Tyr Gln His Asp Arg Thr Ser His Trp Tyr Phe
 1               5                  10                  15
Asp Val
     17

<210> SEQ ID NO 81
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 81

Tyr Pro His Tyr Tyr Val Thr Asp Arg Lys Ser His Trp Tyr Phe
 1               5                  10                  15
Asp Val
     17

<210> SEQ ID NO 82
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 82

Tyr Pro His Tyr Tyr Leu Arg Asp Lys Lys Ser His Trp Tyr Phe
 1               5                  10                  15
Asp Val
     17
```

```
<210> SEQ ID NO 83
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 83

Tyr Pro His Tyr Tyr Ser His Glu Arg Lys Ser His Trp Tyr Phe
 1               5                  10                  15

Asp Val
      17

<210> SEQ ID NO 84
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 84

Tyr Pro His Tyr Tyr Leu Asn Glu Arg Lys Ser His Trp Tyr Phe
 1               5                  10                  15

Asp Val
      17

<210> SEQ ID NO 85
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 85

Tyr Pro His Tyr Tyr Val Asn Glu Arg Lys Ser His Trp Tyr Phe
 1               5                  10                  15

Asp Val
      17

<210> SEQ ID NO 86
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 86

Tyr Pro His Tyr Tyr Leu Thr Asp His Lys Ser His Trp Tyr Phe
 1               5                  10                  15

Asp Val
      17

<210> SEQ ID NO 87
<211> LENGTH: 18
<212> TYPE: PRT
<213> ORGANISM: artificial sequence
<220> FEATURE:
```

```
<221> NAME/KEY: artificial
<222> LOCATION: 1-18
<223> OTHER INFORMATION: variant CDR sequence

<400> SEQUENCE: 87

Tyr Pro His Tyr Tyr Leu Lys Asp Gly Lys Lys Ser His Trp Tyr
 1               5                  10                  15

Phe Asp Val
        18

<210> SEQ ID NO 88
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 88

Tyr Pro His Tyr Tyr Arg Arg Asp Lys Lys Ser His Trp Tyr Phe
 1               5                  10                  15

Asp Val
    17

<210> SEQ ID NO 89
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 89

Tyr Pro His Tyr Tyr Leu Lys Asp Lys Lys Ser His Trp Tyr Phe
 1               5                  10                  15

Asp Val
    17

<210> SEQ ID NO 90
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 90

Tyr Pro His Tyr Tyr Leu His Asp Arg Lys Ser His Trp Tyr Phe
 1               5                  10                  15

Asp Val
    17

<210> SEQ ID NO 91
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 91

Tyr Pro His Tyr Tyr Leu Ser Asp Lys Lys Ser His Trp Tyr Phe
```

```
                   1               5              10              15
Asp Val
      17

<210> SEQ ID NO 92
<211> LENGTH: 17
<212> TYPE: PRT
<213> ORGANISM: artificial sequence
<220> FEATURE:
<221> NAME/KEY: artificial
<222> LOCATION: 1-17
<223> OTHER INFORMATION: variant CDR sequence

<400> SEQUENCE: 92

Tyr Pro His Tyr Tyr Val Asn Glu Arg Lys Ser His Trp Tyr Phe
  1               5                  10                  15

Asp Val
      17

<210> SEQ ID NO 93
<211> LENGTH: 45
<212> TYPE: DNA
<213> ORGANISM: artificial sequence
<220> FEATURE:
<221> NAME/KEY: artificial
<222> LOCATION: 1-45
<223> OTHER INFORMATION: mutagenesis oligo

<400> SEQUENCE: 93
tacccgcact attatgtgaa cgagcggaag agccactggt atttc                          45

<210> SEQ ID NO 94
<211> LENGTH: 110
<212> TYPE: PRT
<213> ORGANISM: artificial sequence
<220> FEATURE:
<221> NAME/KEY: artificial
<222> LOCATION: 1-110
<223> OTHER INFORMATION: humanized antibody light chain variable domain

<400> SEQUENCE: 94

Asp Ile Gln Met Thr Gln Ser Pro Ser Ser Leu Ser Ala Ser Val
  1               5                  10                  15

Gly Asp Arg Val Thr Ile Thr Cys Ser Ala Ser Gln Asp Ile Ser
                 20                  25                  30

Asn Tyr Leu Asn Trp Tyr Gln Gln Lys Pro Gly Lys Ala Pro Lys
                 35                  40                  45

Val Leu Ile Tyr Phe Thr Ser Ser Leu His Ser Gly Val Pro Ser
                 50                  55                  60

Arg Phe Ser Gly Ser Gly Ser Gly Thr Asp Phe Thr Leu Thr Ile
                 65                  70                  75

Ser Ser Leu Gln Pro Glu Asp Phe Ala Thr Tyr Tyr Cys Gln Gln
                 80                  85                  90

Tyr Ser Thr Val Pro Trp Thr Phe Gly Gln Gly Thr Lys Val Glu
                 95                 100                 105

Ile Lys Arg Thr Val
                110

<210> SEQ ID NO 95
<211> LENGTH: 110
<212> TYPE: PRT
<213> ORGANISM: artificial sequence
<220> FEATURE:
```

```
<221> NAME/KEY: artificial
<222> LOCATION: 1-110
<223> OTHER INFORMATION: humanized antibody light chain variable domain

<400> SEQUENCE: 95

Asp Ile Gln Leu Thr Gln Ser Pro Ser Ser Leu Ser Ala Ser Val
  1               5                  10                  15

Gly Asp Arg Val Thr Ile Thr Cys Arg Ala Asn Glu Gln Leu Ser
                20                  25                  30

Asn Tyr Leu Asn Trp Tyr Gln Gln Lys Pro Gly Lys Ala Pro Lys
                35                  40                  45

Val Leu Ile Tyr Phe Thr Ser Ser Leu His Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Tyr Ser Thr Val Pro Trp Thr Phe Gly Gln Gly Thr Lys Val Glu
                95                 100                 105

Ile Lys Arg Thr Val
                110

<210> SEQ ID NO 96
<211> LENGTH: 118
<212> TYPE: PRT
<213> ORGANISM: artificial sequence
<220> FEATURE:
<221> NAME/KEY: artificial
<222> LOCATION: 1-118
<223> OTHER INFORMATION: humanized antibody heavy chain variable domain

<400> SEQUENCE: 96

Glu Val Gln Leu Val Glu Ser Gly Gly Gly Leu Val Gln Pro Gly
  1               5                  10                  15

Gly Ser Leu Arg Leu Ser Cys Ala Ala Ser Gly Tyr Thr Phe Thr
                20                  25                  30

Asn Tyr Gly Met Asn Trp Val Arg Gln Ala Pro Gly Lys Gly Leu
                35                  40                  45

Glu Trp Val Gly Trp Ile Asn Thr Tyr Thr Gly Glu Pro Thr Tyr
                50                  55                  60

Ala Ala Asp Phe Lys Arg Arg Phe Thr Phe Ser Leu Asp Thr Ser
                65                  70                  75

Lys Ser Thr Ala Tyr Leu Gln Met Asn Ser Leu Arg Ala Glu Asp
                80                  85                  90

Thr Ala Val Tyr Tyr Cys Ala Lys Tyr Pro His Tyr Tyr Gly Ser
                95                 100                 105

Ser His Trp Tyr Phe Asp Val Trp Gly Gln Gly Thr Leu
                110                 115        118

<210> SEQ ID NO 97
<211> LENGTH: 118
<212> TYPE: PRT
<213> ORGANISM: artificial sequence
<220> FEATURE:
<221> NAME/KEY: artificial
<222> LOCATION: 1-118
<223> OTHER INFORMATION: humanized antibody heavy chain variable domain

<400> SEQUENCE: 97

Glu Val Gln Leu Val Glu Ser Gly Gly Gly Leu Val Gln Pro Gly
```

```
                1               5                  10                 15
Gly Ser Leu Arg Leu Ser Cys Ala Ala Ser Gly Tyr Asp Phe Thr
                       20                  25                 30
His Tyr Gly Met Asn Trp Val Arg Gln Ala Pro Gly Lys Gly Leu
                       35                  40                 45
Glu Trp Val Gly Trp Ile Asn Thr Tyr Thr Gly Glu Pro Thr Tyr
                       50                  55                 60
Ala Ala Asp Phe Lys Arg Arg Phe Thr Phe Ser Leu Asp Thr Ser
                       65                  70                 75
Lys Ser Thr Ala Tyr Leu Gln Met Asn Ser Leu Arg Ala Glu Asp
                       80                  85                 90
Thr Ala Val Tyr Tyr Cys Ala Lys Tyr Pro His Tyr Tyr Gly Ser
                       95                 100                105
Ser His Trp Tyr Phe Asp Val Trp Gly Gln Gly Thr Leu
                      110                 115       118

<210> SEQ ID NO 98
<211> LENGTH: 121
<212> TYPE: PRT
<213> ORGANISM: artificial sequence
<220> FEATURE:
<221> NAME/KEY: artificial
<222> LOCATION: 1-121
<223> OTHER INFORMATION: humanized antibody heavy chain variable domain

<400> SEQUENCE: 98

Glu Val Gln Leu Val Glu Ser Gly Gly Gly Leu Val Gln Pro Gly
                1               5                  10                 15
Gly Ser Leu Arg Leu Ser Cys Ala Ala Ser Gly Tyr Thr Phe Thr
                       20                  25                 30
Asn Tyr Gly Met Asn Trp Val Arg Gln Ala Pro Gly Lys Gly Leu
                       35                  40                 45
Glu Trp Val Gly Trp Ile Asn Thr Tyr Thr Gly Glu Pro Thr Tyr
                       50                  55                 60
Ala Ala Asp Phe Lys Arg Arg Phe Thr Phe Ser Leu Asp Thr Ser
                       65                  70                 75
Lys Ser Thr Ala Tyr Leu Gln Met Asn Ser Leu Arg Ala Glu Asp
                       80                  85                 90
Thr Ala Val Tyr Tyr Cys Ala Lys Tyr Pro His Tyr Tyr Val Asn
                       95                 100                105
Glu Arg Lys Ser His Trp Tyr Phe Asp Val Trp Gly Gln Gly Thr
                      110                 115                120
Leu
121

<210> SEQ ID NO 99
<211> LENGTH: 121
<212> TYPE: PRT
<213> ORGANISM: artificial sequence
<220> FEATURE:
<221> NAME/KEY: artificial
<222> LOCATION: 1-121
<223> OTHER INFORMATION: humanized antibody heavy chain variable domain

<400> SEQUENCE: 99

Glu Val Gln Leu Val Glu Ser Gly Gly Gly Leu Val Gln Pro Gly
                1               5                  10                 15
Gly Ser Leu Arg Leu Ser Cys Ala Ala Ser Gly Tyr Asp Phe Thr
                       20                  25                 30
```

-continued

```
His Tyr Gly Met Asn Trp Val Arg Gln Ala Pro Gly Lys Gly Leu
                 35                  40                  45

Glu Trp Val Gly Trp Ile Asn Thr Tyr Thr Gly Glu Pro Thr Tyr
                 50                  55                  60

Ala Ala Asp Phe Lys Arg Arg Phe Thr Phe Ser Leu Asp Thr Ser
                 65                  70                  75

Lys Ser Thr Ala Tyr Leu Gln Met Asn Ser Leu Arg Ala Glu Asp
                 80                  85                  90

Thr Ala Val Tyr Tyr Cys Ala Lys Tyr Pro His Tyr Tyr Val Asn
                 95                 100                 105

Glu Arg Lys Ser His Trp Tyr Phe Asp Val Trp Gly Gln Gly Thr
                110                 115                 120

Leu
121
```

ANTIBODY VARIANTS

This is a non-provisional application filed under 37 CFR 1.53(b) claiming priority to provisional application No. 60/108,945 filed Nov. 18, 1998, the contents of which are incorporated herein by reference.

BACKGROUND OF THE INVENTION

1. Field of the Invention

This invention relates generally to antibody variants. In particular, antibody variants of parent antibodies are disclosed which have one or more amino acids inserted in a hypervariable region of the parent antibody and a binding affinity for a target antigen which is at least about two fold stronger than the binding affinity of the parent antibody for the antigen.

2. Description of Related Art

Antibodies are proteins, which exhibit binding specificity to a specific antigen. Native antibodies are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains.

The term "variable" refers to the fact that certain portions of the variable domains differ extensively in sequence among antibodies and are responsible for the binding specificity of each particular antibody for its particular antigen. However, the variability is not evenly distributed through the variable domains of antibodies. It is concentrated in three segments called Complementarity Determining Regions (CDRs) both in the light chain and the heavy chain variable domains. The more highly conserved portions of the variable domains are called the framework regions (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies (see Kabat et al., *Sequences of Proteins of Immunological Interest*, 5th Ed. Public Health Service, National Institutes of Health, Bethesda, MD. (1991)).

The constant domains are not involved directly in binding an antibody to an antigen, but exhibit various effector functions. Depending on the amino acid sequence of the constant region of their heavy chains, antibodies or immunoglobulins can be assigned to different classes. There are five major classes of immunoglobulins: IgA, IgD, IgE, IgG and IgM, and several of these may be further divided into subclasses (isotypes), e.g. IgG1, IgG2, IgG3, and IgG4; IgA1 and IgA2. The heavy chain constant regions that correspond to the different classes of immunoglobulins are called a, α, δ, ε, γ, and μ, respectively. Of the various human immunoglobulin classes, only human IgG1, IgG2, IgG3 and IgM are known to activate complement.

In vivo, affinity maturation of antibodies is driven by antigen selection of higher affinity antibody variants which are made primarily by somatic hypermutagenesis. A "repertoire shift" also often occurs in which the predominant germline genes of the secondary or tertiary response are seen to differ from those of the primary or secondary response.

Various research groups have attempted to mimic the affinity maturation process of the immune system, by introducing mutations into antibody genes in vitro and using affinity selection to isolate mutants with improved affinity. Such mutant antibodies can be displayed on the surface of filamentous bacteriophage and antibodies can be selected by their affinity for antigen or by their kinetics of dissociation (off-rate) from antigen. Hawkins et al. *J. Mol. Biol.* 226:889–896 (1992). CDR walking mutagenesis has been employed to affinity mature human antibodies which bind the human envelope glycoprotein gp120 of human immunodeficiency virus type 1 (HIV-1) (Barbas III et al. *PNAS (USA)* 91: 3809–3813 (1994); and Yang et al. *J. Mol. Biol.* 254:392–403 (1995)); and an anti-c-erbB-2 single chain Fv fragment (Schier et al. *J. Mol. Biol.* 263:551567 (1996)). Antibody chain shuffling and CDR mutagenesis were used to affinity mature a high-affinity human antibody directed against the third hypervariable loop of HIV (Thompson et al. *J. Mol. Biol.* 256:77–88 (1996)). Balint and Larrick Gene 137:109–118 (1993) describe a technique they coin "parsimonious mutagenesis" which involves computer-assisted oligodeoxyribonucleotide-directed scanning mutagenesis whereby all three CDRs of a variable region gene are simultaneously and thoroughly searched for improved variants. Wu et al. affinity matured an αvβ3-specific humanized antibody using an initial limited mutagenesis strategy in which every position of all six CDRs was mutated followed by the expression and screening of a combinatorial library including the highest affinity mutants (Wu et al. *PNAS (USA)* 95: 6037-6-42 (1998)). Phage antibodies are reviewed in Chiswell and McCafferty *TIBTECH* 10:80–84 (1992); and Rader and Barbas III *Current Opinion in Biotech.* 8:503–508 (1997). In each case where mutant antibodies with improved affinity compared to a parent antibody are reported in the above references, the mutant antibody has amino acid substitutions in a CDR.

SUMMARY OF THE INVENTION

Unlike the affinity matured antibodies of the above references, the present invention provides an antibody variant of a parent antibody, which antibody variant comprises an amino acid insertion in or adjacent to a hypervariable region of the parent antibody and has a binding affinity for a target antigen which is at least about two fold stronger than the binding affinity of the parent antibody for the antigen.

The invention further provides an antibody variant comprising a heavy chain variable domain, wherein CDR H3 of the heavy chain variable domain comprises the amino acid sequence of CDR H3 of a variant selected from the group consisting of Y0239-19 (SEQ ID NO:85); Y0239-8 (SEQ ID NO:53); Y0240-1 (SEQ ID NO:86); Y0239-12 (SEQ ID NO:78); Y0239-9 (SEQ ID NO:54); and Y0261-6 (SEQ ID NO:89). These CDR H3 sequences may, for example, be provided in the heavy chain variable domain sequence of SEQ ID NO: 98 or 99; see FIG. 1B). Preferably, the antibody variant further comprises a light chain variable domain and binds VEGF antigen with stronger binding affinity than Y0192 (see FIGS. 1A and 1B; SEQ ID NO's 95 and 96).

The invention further provides a method for producing an antibody variant comprising introducing an amino acid residue in or adjacent to a hypervariable region of a parent antibody, wherein the antibody variant has a binding affinity for a target antigen which is at least about two fold stronger than the binding affinity of the parent antibody for said antigen.

Additionally, the invention provides a method for making an antibody variant, comprising the steps of:

(a) identifying potential amino acid interactions between a hypervariable region of a parent antibody and a target antigen;

(b) preparing a variant of the parent antibody comprising introducing an amino acid residue in or adjacent to the hypervariable region of the parent antibody, wherein the introduced amino acid residue contributes to the potential amino acid interactions in (a); and (c) selecting an antibody variant prepared as in (b) which has a stronger binding affinity for the antigen than the parent antibody.

Various forms of the antibody variant are contemplated herein. For example, the antibody variant may be a full length antibody (e.g. having a human immunoglobulin constant region) or an antibody fragment (e.g. a F(ab')$_2$). Furthermore, the antibody variant may be labeled with a detectable label, immobilized on a solid phase and/or conjugated with a heterologous compound (such as a cytotoxic agent).

Diagnostic and therapeutic uses for the antibody variant are contemplated. In one diagnostic application, the invention provides a method for determining the presence of an antigen of interest comprising exposing a sample suspected of containing the antigen to the antibody variant and determining binding of the antibody variant to the sample. For this use, the invention provides a kit comprising the antibody variant and instructions for using the antibody variant to detect the antigen.

The invention further provides: isolated nucleic acid encoding the antibody variant; a vector comprising the nucleic acid, optionally, operably linked to control sequences recognized by a host cell transformed with the vector; a host cell transformed with the vector; a process for producing the antibody variant comprising culturing this host cell so that the nucleic acid is expressed and, optionally, recovering the antibody variant from the host cell culture (e.g. from the host cell culture medium).

The invention also provides a composition comprising the antibody variant and a pharmaceutically acceptable carrier or diluent. This composition for therapeutic use is sterile and may be lyophilized.

The invention further provides a method for treating a mammal comprising administering an effective amount of the antibody variant to the mammal.

BRIEF DESCRIPTION OF THE DRAWINGS

FIGS. 1A and 1B show a sequence alignment of the light chain variable region (FIG. 1A) and heavy chain variable region (FIG. 1B) of several variants of the humanized anti-VEGF antibody F(ab)-12. The parental Fab-phage clone Y0192 contains light chain mutations which do not significantly affect antigen binding affinity, and has been described (WO98/45331). Another variant, Y0238-3, contains mutations in CDR H1 which improve antigen-binding (WO98/45331). Variant Y0239-19 contains the "VNERK" motif identified in selections from CDR H3 insertion libraries described herein. Variant Y0313-2 contains the CDR H1 mutations of Y0238-3 combined with the CDR H3 mutations of Y0239-19. Differences from F(ab)-12 are highlighted with shaded boxes. The sequence identifiers in FIGS. 1A and 1B are as follows: F(ab)-12 light chain variable domain (SEQ ID NO:94); Y0192, Y0238-3, Y0239-19 and Y0313-2 light chain variable domain (SEQ ID NO:95); F(ab)-12 and Y0192 heavy chain variable domain (SEQ ID NO:96); Y0238-3 heavy chain variable domain (SEQ ID NO:97); Y0239-19 heavy chain variable domain (SEQ ID NO:98); and Y0313-2 heavy chain variable domain (SEQ ID NO:99).

FIG. 2 shows the inhibition of VEGF activity in a cell-based bioassay by Fab, F(ab)-12 and Fab variant Y0313-2.

DETAILED DESCRIPTION OF THE PREFERRED EMBODIMENTS

I. Definitions

Figure 3:
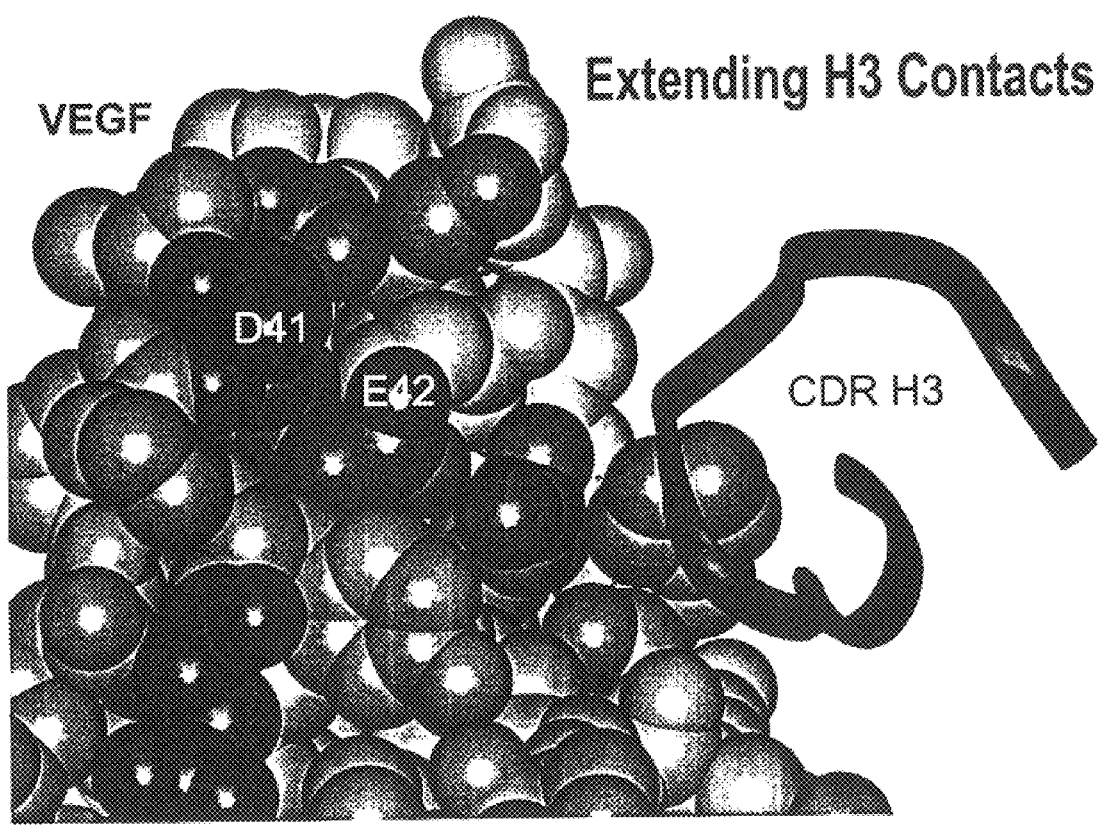
FIG. 3 shows a portion of the three-dimensional model of F(ab)-12 in complex with VEGF as determined by x-ray crystallography (Muller et al. *Structure* 6(9): 1153–1167 (1998)). The main chain trace of the CDR H3 region of the antibody is depicted as a magenta ribbon at right. A surface rendering of a portion of VEGF is depicted at left, with several proximal residues highlighted in red (acidic) or purple (basic). The side chain of D41 of VEGF can be seen as a site of potential interaction with a hypothetical insertion peptide placed into the CDR H3.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

The term "hypervariable region" when used herein refers to the regions of an antibody variable domain which are hypervariable in sequence and/or form structurally defined loops. The hypervariable region comprises amino acid residues from a "complementarity determining region" or "CDR" (i.e. residues 24–34 ("CDR L1"), 50–56 ("CDR L2") and 89–97 ("CDR L3") in the light chain variable domain and 31–35 ("CDR H1"), 50–65 ("CDR H2") and 95–102 ("CDR H3") in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (i.e. residues 26–32 ("loop L1"), 50–52 ("loop L2") and 91–96 ("loop L3") in the light chain variable domain and 26–32 ("loop H1"), 53–55 ("loop H2") and 96–101 ("loop H3") in the heavy chain variable domain; Chothia and Lesk *J. Mol. Biol.* 196:901–917 (1987)). In both cases, the variable domain residues are numbered according to Kabat et al., supra. "Framework" or "FR" residues are those variable domain residues other than the hypervariable region residues as herein defined.

The expression "variable domain residue numbering as in Kabat" refers to the numbering system used for heavy chain variable domains or light chain variable domains of the compilation of antibodies in Kabat et al., *Sequences of Proteins of Immunological Interest*, 5th Ed. Public Health Service, National Institutes of Health, Bethesda, MD. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of CDR H2 and inserted residues (e.g. residues 82a, 82b, and 82c, etc according to Kabat) after heavy chain FR residue 82. The Kabat numbering of residues may be determined for a given antibody by alignment at regions of homology of the sequence of the antibody with a "standard" Kabat numbered sequence.

"Antibody fragments" comprise a portion of a full length antibody, generally the antigen binding or variable region thereof. Examples of antibody fragments include Fab, Fab', F(ab')$_2$, and Fv fragments; diabodies; linear antibodies; single-chain antibody molecules; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature* 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature* 352:624–628 (1991) and Marks et al., *J. Mol. Biol.* 222:581–597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851–6855 (1984)). "Humanized" forms of non-human (e.g., murine) antibodies are chimeric antibodies which contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., *Nature* 321:522–525 (1986); Riechmann et al., *Nature* 332:323–329 (1988); and Presta, *Curr. Op. Struct. Biol.* 2:593–596 (1992). "Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv see Pluckthun in *The Pharmacology of Monoclonal Antibodies*, vol. 113, Rosenburg and Moore eds. Springer-Verlag, New York, pp. 269–315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA* 90:6444–6448 (1993).

The expression "linear antibodies" when used throughout this application refers to the antibodies described in Zapata et al. Protein Eng. 8(10):1057–1062 (1995). Briefly, these antibodies comprise a pair of tandem Fd segments ($V_H$-$C_H$1-$V_H$-$C_H$1) which form a pair of antigen binding regions. Linear antibodies can be bispecific or monospecific.

A "parent antibody" is an antibody comprising an amino acid sequence which lacks, or is deficient in, one or more amino acid residues in or adjacent to one or more hypervariable regions thereof compared to an antibody variant as herein disclosed. Thus, the parent antibody has a shorter hypervariable region than the corresponding hypervariable region of an antibody variant as herein disclosed. The parent polypeptide may comprise a native sequence (i.e. a naturally occurring) antibody (including a naturally-occurring allelic variant) or an antibody with pre-existing amino acid sequence modifications (such as other insertions, deletions and/or substitutions) of a naturally-occurring sequence. Preferably the parent antibody is a humanized antibody or a human antibody.

As used herein, "antibody variant" refers to an antibody which has an amino acid sequence which differs from the amino acid sequence of a parent antibody. Preferably, the antibody variant comprises a heavy chain variable domain or a light chain variable domain having an amino acid sequence which is not found in nature. Such variants necessarily have less than 100% sequence identity or similarity with the parent antibody. In a preferred embodiment, the antibody variant will have an amino acid sequence from about 75% to less than 100% amino acid sequence identity or similarity with the amino acid sequence of either the heavy or light chain variable domain of the parent antibody, more preferably from about 80% to less than 100%, more preferably from about 85% to less than 100%, more preferably from about 90% to less than 100%, and most preferably from about 95% to less than 100%. Identity or similarity with respect to this sequence is defined herein as the percentage of amino acid residues in the candidate sequence that are identical (i.e same residue) with the parent antibody residues, after aligning the sequences and introducing gaps, if necessary, to achieve the maximum percent sequence identity. None of N-terminal, C-terminal, or internal extensions, deletions, or insertions into the antibody sequence outside of the variable domain shall be construed as affecting sequence identity or similarity. The antibody variant is generally one which has a longer hypervariable region (by one or more amino acid residues; e.g. by about one to about 30 amino acid residues and preferably by about two to about ten amino acid residues) than the corresponding hypervariable region of a parent antibody.

An "amino acid alteration" refers to a change in the amino acid sequence of a predetermined amino acid sequence. Exemplary alterations include insertions, substitutions and deletions.

An "amino acid insertion" refers to the introduction of one or more amino acid residues into a predetermined amino acid sequence The amino acid insertion may comprise a "peptide insertion" in which case a peptide comprising two or more amino acid residues joined by peptide bond(s) is introduced into the predetermined amino acid sequence. Where the amino acid insertion involves insertion of a peptide, the inserted peptide may be generated by random mutagenesis such that it has an amino acid sequence which does not exist in nature.

The inserted residue or residues may be "naturally occurring amino acid residues" (i.e. encoded by the genetic code) and selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (Ile): leucine (Leu); lysine (Lys); methionine (Met); phenylalanine (Phe); proline (Pro); serine (Ser); threonine (Thr); tryptophan (Trp); tyrosine (Tyr); and valine (Val).

Insertion of one or more non-naturally occurring amino acid residues is also encompassed by the definition of an amino acid insertion herein. A "non-naturally occurring amino acid residue" refers to a residue, other than those naturally occurring amino acid residues listed above, which is able to covalently bind adjacent amino acid residues(s) in a polypeptide chain. Examples of non-naturally occurring amino acid residues include norleucine, ornithine, norvaline, homoserine and other amino acid residue analogues such as those described in Ellman et al. *Meth. Enzym.* 202:301–336 (1991). To generate such non-naturally occurring amino acid residues, the procedures of Noren et al. *Science* 244:182 (1989) and Ellman et al., supra, can be used. Briefly, these procedures involve chemically activating a suppressor tRNA with a non-naturally occurring amino acid residue followed by in vitro transcription and translation of the RNA.

An amino acid insertion "in a hypervariable region" refers to the introduction of one or more amino acid residues within a hypervariable region amino acid sequence.

An amino acid insertion "adjacent a hypervariable region" refers to the introduction of one or more amino acid residues at the N-terminal and/or C-terminal end of a hypervariable region, such that at least one of the inserted amino acid residues forms a peptide bond with the N-terminal or C-terminal amino acid residue of the hypervariable region in question.

An "amino acid substitution" refers to the replacement of an existing amino acid residue in a predetermined amino acid sequence with another different amino acid residue.

The term "potential amino acid interactions" refers to contacts or energetically favorable interactions between one or more amino acid residues present in an antigen and one or more amino acid residues which do not exist in a parent antibody but can be introduced therein so as to increase the amino acid contacts between the antigen and an antibody variant comprising those introduced amino acid residue(s). Preferably the the amino acid interactions of interest are selected from the group consisting of hydrogen bonding, van der Waals interactions and ionic interactions The term "target antigen" herein refers to a predetermined antigen to which both a parent antibody and antibody variant as herein defined bind. The target antigen may be polypeptide, carbohydrate, nucleic acid, lipid, hapten or other naturally occurring or synthetic compound. Preferably, the target antigen is a polypeptide. While the antibody variant binds the target antigen with better binding affinity than the parent antibody, the parent antibody generally has a binding affinity ($K_d$) value for the target antigen of no more than about $1\times10^{-5}$M , and preferably no more than about $1\times10^{-6}$M.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

"Treatment" refers to both therapeutic treatment and prophylactic or preventative measures. Those in need of treatment include those already with the disorder as well as those in which the disorder is to be prevented.

A "disorder" is any condition that would benefit from treatment with the antibody variant. This includes chronic and acute disorders or diseases including those pathological conditions which predispose the mammal to the disorder in question.

"Mammal" for purposes of treatment refers to any animal classified as a mammal, including humans, domestic and farm animals, nonhuman primates, and zoo, sports, or pet animals, such as dogs, horses, cats, cows, etc.

The term "cytotoxic agent" as used herein refers to a substance that inhibits or prevents the function of cells and/or causes destruction of cells. The term is intended to include radioactive isotopes (e.g., $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include Adriamycin, Doxorubicin, 5-Fluorouracil, Cytosine arabinoside ("Ara-C"), Cyclophosphamide, Thiotepa, Taxotere (docetaxel), Busulfan, Cytoxin, Taxol, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Carminomycin, Aminopterin, Dactinomycin, Mitomycins, Esperamicins (see U.S. Pat. No. 4,675,187), Melphalan and other related nitrogen mustards.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" *Biochemical Society Transactions*, 14, pp. 375–382, 615th Meeting Belfast (1986) and Stella et al., "*Prodrugs: A Chemical Approach to Targeted Drug Delivery,*" Directed Drug Delivery, Borchardt et al., (ed.), pp. 247–267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

The word "label" when used herein refers to a detectable compound or composition which is conjugated directly or indirectly to the antibody. The label may be itself be detectable (e.g., radioisotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g. controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g. an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as the antibody variants disclosed herein and, optionally, a chemotherapeutic agent) to a mammal. The components of the liposome are commonly arranged in a bilayer formation, similar to the lipid arrangement of biological membranes.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

II. Modes for Carrying out the Invention

The invention herein relates to a method for making an antibody variant. The parent antibody or starting antibody is prepared using techniques available in the art for generating such antibodies. Exemplary methods for generating antibodies are described in more detail in the following sections.

The parent antibody is directed against a target antigen of interest. Preferably, the target antigen is a biologically important polypeptide and administration of the antibody to a mammal suffering from a disease or disorder can result in a therapeutic benefit in that mammal. However, antibodies directed against nonpolypeptide antigens (such as tumor-associated glycolipid antigens; see U.S. Pat. No. 5,091,178) are also contemplated.

Where the antigen is a polypeptide, it may be a transmembrane molecule (e.g. receptor) or ligand such as a growth factor. Exemplary antigens include molecules such as renin; a growth hormone, including human growth hormone and bovine growth hormone; growth hormone releasing factor; parathyroid hormone; thyroid stimulating hormone; lipoproteins; alpha-l-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor; platelet-derived growth factor (PDGF); fibroblast growth factor such as aFGF and bFGF; epidermal growth factor (EGF); transforming growth factor (TGF) such as TGF-alpha and TGF-beta; insulin-like growth factor-I and -II (IGF-I and IGF-II); des(1–3)-IGF-I (brain IGF-I), insulin-like growth factor binding proteins; CD proteins such as CD3, CD4, CD8, CD19 and CD20; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as HER2, HER3 or HER4 receptor; and fragments of any of the above-listed polypeptides.

Preferred molecular targets for antibodies encompassed by the present invention include CD proteins such as CD3, CD4, CD8, CD19, CD20 and CD34; members of the ErbB receptor family such as the EGF receptor, HER2, HER3 or HER4 receptor; cell adhesion molecules such as LFA-1, Macl, p150,95, VLA-4, ICAM-1, VCAM and αvβ3 integrin including either alpha or beta subunits thereof (e.g. anti-CD11a, anti-CD18 or anti-CD11b antibodies); growth factors such as VEGF; IgE; blood group antigens; flk2/flt3 receptor; obesity (OB) receptor; mpl receptor; CTLA-4; protein C etc.

The antigen used to generate an antibody may be isolated from a natural source thereof, or may be produced recombinantly or made using other synthetic methods. Alternatively, cells comprising native or recombinant antigen can be used as immunogens for making antibodies.

The parent antibody may have pre-existing strong binding affinity for the target antigen. For example, the parent antibody may bind the antigen of interest with a binding affinity ($K_d$) value of no more than about $1 \times 10^{-7}$ M, preferably no more than about $1 \times 10^{-8}$ M and most preferably no more than about $1 \times 10^{-9}$ M.

Antibody "binding affinity" may be determined by equilibrium methods (e.g. enzyme-linked immunoabsorbent assay (ELISA) or radioimmunoassay (RIA)), or kinetics (e.g. BIACORE™ analysis; see Example 1 below), for example.

Also, the antibody may be subjected to other "biological activity assays", e.g., in order to evaluate its "potency" or pharmacological activity and potential efficacy as a therapeutic agent. Such assays are known in the art and depend on the target antigen and intended use for the antibody. Examples include the keratinocyte monolayer adhesion assay and the mixed lymphocyte response (MLR) assay for CD11a (see WO98/23761); tumor cell growth inhibition assays (as described in WO 89/06692, for example); antibody-dependent cellular cytotoxicity (ADCC) and complement-mediated cytotoxicity (CDC) assays (U.S. Pat. No. 5,500,362); agonistic activity or hematopoiesis assays (see WO 95/27062); tritiated thymidine incorporation assay; and alamar blue assay to measure metabolic activity of cells in response to a molecule such as VEGF (See Example 1 below).

The amino acid sequence of the parent antibody is altered so as to generate an antibody variant which has a stronger binding affinity for the target antigen than the parent antibody. The antibody variant preferably has a binding affinity for the target antigen which is at least about two fold stronger (e.g. from about two fold to about 1000 fold or even to about 10,000 fold improved binding affinity), preferably at least about five fold stronger, and preferably at least about ten fold or 100 fold stronger, than the binding affinity of the parent antibody for the antigen. The enhancement in binding affinity desired or required may depend on the initial binding affinity of the parent antibody.

Where the assay used is a biological activity assay, the antibody variant preferably has a potency in the biological activity assay of choice which is at least about two fold greater (e.g. from about two fold to about 1000 fold or even to about 10,000 fold improved potency), preferably at least about 20 fold greater, more preferably at least about 50 fold greater, and sometimes at least about 100 fold or 200 fold greater, than the biological activity of the parent antibody in that assay.

To generate the antibody variant, one or more amino acid residues are introduced or inserted in or adjacent to one or more of the hypervariable regions of the parent antibody. Generally, one will insert one or more amino acid residues in a CDR of the parent antibody. The number of residues to be inserted may be from about one residue to about 30 amino acid residues, e.g. from about two to about ten amino acid residues. In deciding the number of residues to be inserted, one may take into account the range of lengths of the hypervariable region in question in known antibodies. For example, for the first hypervariable region of a light chain variable domain, the hypervariable region is preferably "CDR L1" according to Kabat et al., supra, e.g. having an overall length from about nine amino acid residues to about 20 residues, including the inserted amino acid residue(s). With respect to the second hypervariable region of a light chain variable domain, the hypervariable region is preferably "CDR L2" according to Kabat et al., supra, e.g. having an overall length from about five amino acid residues to about ten residues, including the inserted amino acid residue(s). In relation to the third hypervariable region of a light chain variable domain, the hypervariable region is preferably "CDR L3" according to Kabat et al., supra, e.g. having an overall length from about seven amino acid residues to about 20 residues, including the inserted amino acid residue(s).

Preferably, the antibody variant has one or more amino acid residues inserted in a hypervariable region of the heavy chain variable region, most preferably CDR H3. If this hypervariable region is chosen, preferably the inserted amino acid residues are between residue numbers 97 and 102 (e.g., adjacent to, and preferably C-terminal in sequence to, residue number 100) of the heavy chain variable domain of the parent antibody, utilizing the variable domain residue numbering as in Kabat.

In deciding upon the number of amino acid residues to insert, one may take into account the desired length of the altered hypervariable region. For example, for the first hypervariable region of a heavy chain variable domain, the hypervariable region is preferably the stretch of residues from the "loop H1" of Chothia et al, supra, combined with the stretch of residues considered to constitute "CDR H1" according to Kabat et al., supra. Thus, this first hypervariable loop of the heavy chain variable domain may have an overall length from about eight amino acid residues to about 20 residues including the inserted amino acid residue(s). In relation to the second hypervariable region of a heavy chain variable domain, the hypervariable region is preferably "CDR H2" according to Kabat et al., supra, e.g. having an overall length from about 14 amino acid residues to about 25 residues, including the inserted amino acid residue(s). Finally, in relation to the third hypervariable region of a heavy chain variable domain, the hypervariable region is preferably "CDR H3" according to Kabat et al., supra, e.g. having an overall length from about six amino acid residues to about 30 residues, including the inserted amino acid residue(s).

Antibody variants with inserted amino acid residue(s) in a hypervariable region thereof may be prepared randomly, especially where the starting binding affinity of the parent antibody for the target antigen is such that randomly produced antibody variants can be readily screened. For example, phage display provides a convenient method of screening such random variants.

The invention also provides a more systematic method for making antibody variants. This method involves the following general steps, usually performed sequentially:

(a) identifying potential amino acid interactions between a hypervariable region of a parent antibody and a target antigen;

(b) preparing a variant of the parent antibody by introducing an amino acid residue in or adjacent to the hypervariable region of the parent antibody, wherein the introduced amino acid residue contributes to the potential amino acid interactions in (a); and (c) selecting an antibody variant prepared as in (b) which has a stronger binding affinity for the antigen than the parent antibody.

According to step (a) of this method, one may analyze a molecular model of the parent antibody complexed with antigen. The molecular model may be obtained from an X-ray crystal or nuclear magnetic resonance (NMR) structure of this complex. See, e.g., Amit et al. *Science* 233:747–753 (1986); and Muller et al. *Structure* 6(9): 1153–1167 (1998)). Alternatively, computer programs can be used to create molecular models of antibody/antigen complexes (see, e.g., Levy et al. *Biochemistry* 28:7168–7175 (1989); Bruccoleri et al. *Nature* 335: 564–568 (1998); and Chothia et al. *Science* 233: 755–758 (1986)), where a crystal structure is not available.

In the preferred method, one analyzes the molecular model of the antigen/antibody complex and identifies potential areas for increasing energetically favorable interactions between the antigen and a hypervariable region of the antibody. For example, one may identify potential polar interactions (e.g. ion pairs and/or hydrogen-bonding); non-polar interactions (such as Van der Waals attractions and/or hydrophobic interactions); and/or covalent interactions (e.g. disulfide bond(s)) between one or more amino acid residues of the antigen and one or more amino acid residues which can be inserted in or adjacent to a hypervariable region of the antibody. Preferably at least one of the inserted residues has a net positive charge or a net negative charge. For example, at least one of the inserted residues may be a positively charged residue, preferably arginine or lysine.

Examples of side chains typically having positive charge are lysine, arginine, and histidine. Examples of side chains typically having negative charge are aspartic acid and glutamic acid. These side chains may undergo ionic interactions (positive residues paired with negative residues), as well as polar interactions with side chains having polar functional groups: tryptophan, serine, threonine, tyrosine, cysteine, tyrosine, asparagine, and glutamine. In addition, polar or ionic interactions may be mediated through intervening solvent (such as water) or solute (e.g. phosphate or sulfate) molecules.

Examples of residues which may be involved in hydrophobic interactions, or non-polar Van der Waals interactions, are typically alanine, valine, leucine, isoleucine, proline, phenylalanine, tryptophan, methionine, and tyrosine; however, the non-polar side chains of other residues, such as lysine or arginine, may also participate in such interactions. Aromatic side chains such as phenylalanine, tyrosine, and tryptophan may form aromatic (pi) stacking interactions, or may act as hydrogen-bond acceptors.

In addition, the main chain atoms of any residue (including glycine) may undergo Van der Waals or hydrophobic interactions; and the atoms nitrogen and carbonyl oxygen of the main chain, may undergo polar (hydrogen-bonding) interactions. In some cases, a covalent bond (disulfide) may be formed from a cysteine residue of the antibody with a cysteine residue of the antigen.

Finally, post-translational modifications (e.g., glycosylation or phosphorylation) or a prosthetic group (e.g., heme or zinc finger) may provide additional functional groups (carboxylate or phosphate oxygens; zinc or iron atoms) for interaction between antibody and antigen.

Thus, one may, for example, introduce one or more charged amino acid residues in or adjacent to a hypervariable region of the parent antibody in an appropriate three dimensional location, such that the introduced residue or residues are able to form ion pair(s) with one or more oppositely charged residues in the antigen. Similarly, one can create hydrogen-bonding pair(s), Van der Waals interactions, etc., by introducing appropriate amino acid residues in an appropriate location in or adjacent to a hypervariable region of the antibody.

The antibody variant may comprise additional alterations, such as amino acid deletions or substitutions in the hypervariable region of the antibody in which the insertion is made. This is shown in the example below, wherein the hypervariable region was modified by both amino acid substitutions as well as amino acid insertions.

In general, any inserted amino acid residue or inserted peptide will need to exit the existing antibody polypeptide chain at a residue position (x), extend to a point sufficiently near to the site of a new contact such that some portion of the amino acid side chain or main chain of the peptide can form an interaction, and return to reenter the existing antibody polypeptide chain at a position (y) (where y>x in the linear sequence).

It is desirable that the inserted amino acid residue or peptide not significantly perturb the structure of the antibody in a global or local sense, beyond the vicinity of the newly inserted amino acid residue or peptide. In particular, the inserted amino acid residue or peptide preferably does not distort the FR residues of the antibody, or residues of the antibody or antigen involved in existing contacts. This may be evaluated in an actual or modeled complex.

If both exit/reentry residues (x and y) lack significant intramolecular and intermolecular contacts (i.e., both within the antibody, and between antibody and antigen), then an amino acid or peptide insertion may be accomplished by adding a peptide segment between residues x and y, leaving residues x and y unchanged. Alternatively, either or both residues x and y may be deleted and 10 replaced by a peptide segment of >2 residues.

Often, residues x and y, and/or intervening residues in the parent antibody, may be involved in significant intramolecular and intermolecular contacts. In this case, these interactions may be maintained or replaced with residues contributing similar interactions, while allowing for an inserted residue or peptide to exit and reenter the chain. This may be accomplished by substituting the two residues x and y and/or intervening residues in the parent antibody with random residues, which can be subsequently subjected to affinity screening (or screening for other biological activities) to identify variants with improved affinity.

This systematic method is illustrated in FIG. 3 for example, where residues D41 and E42 in the VEGF antigen were identified as potential candidates for interacting with introduced residues in CDR H3 of the heavy chain variable domain of the parent antibody.

Figure 4:
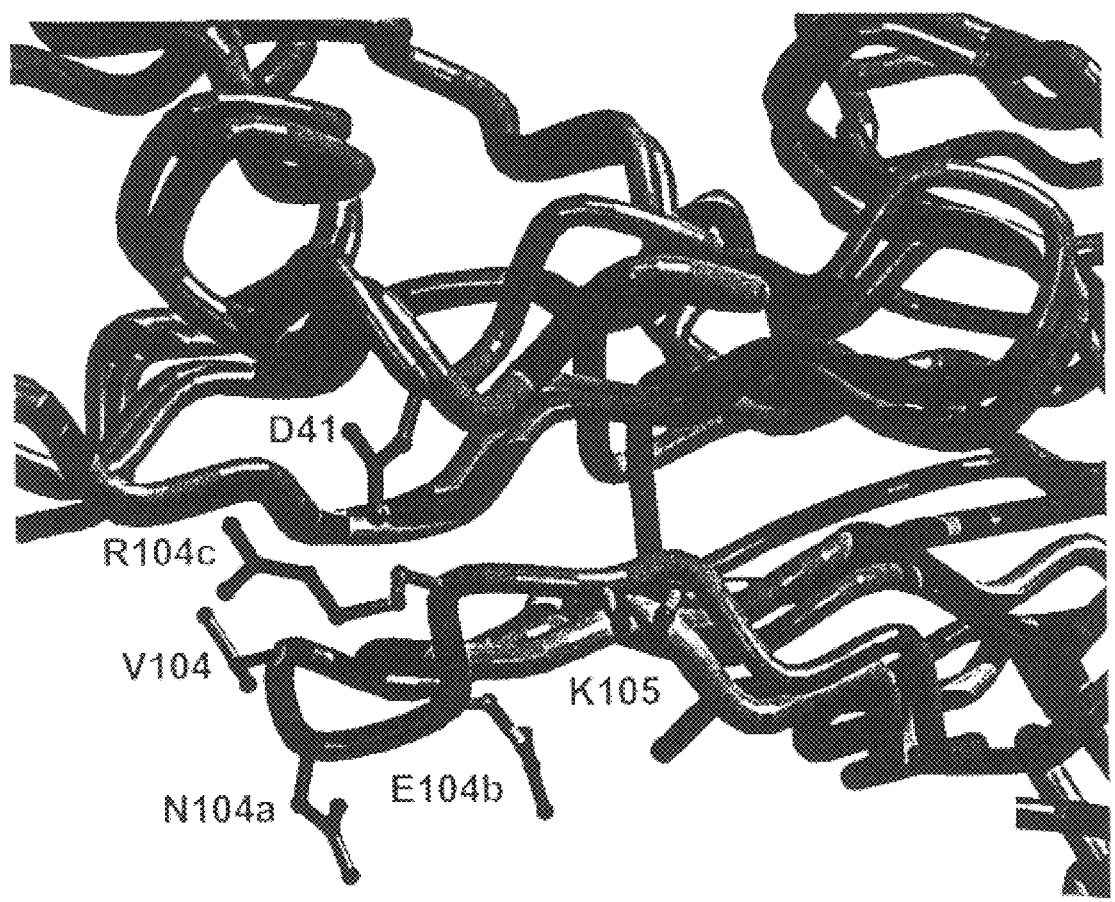
FIG. 4 shows a superposition of portions of the three-dimensional model of F(ab)-12 in complex with VEGF (both molecules in gray; Muller et al., supra) with a model of the insertion variant Fab Y0313-2 (green) in complex with VEGF (yellow). The latter model is based on x-ray crystallographic determination of the variant complex structure described herein. The figure illustrates that little structural change is observed in the complex as compared with the F(ab)-12 complex, except in the immediate vicinity of the mutations V104, N104a, E104b, R104c, and K105.
Figure 5:
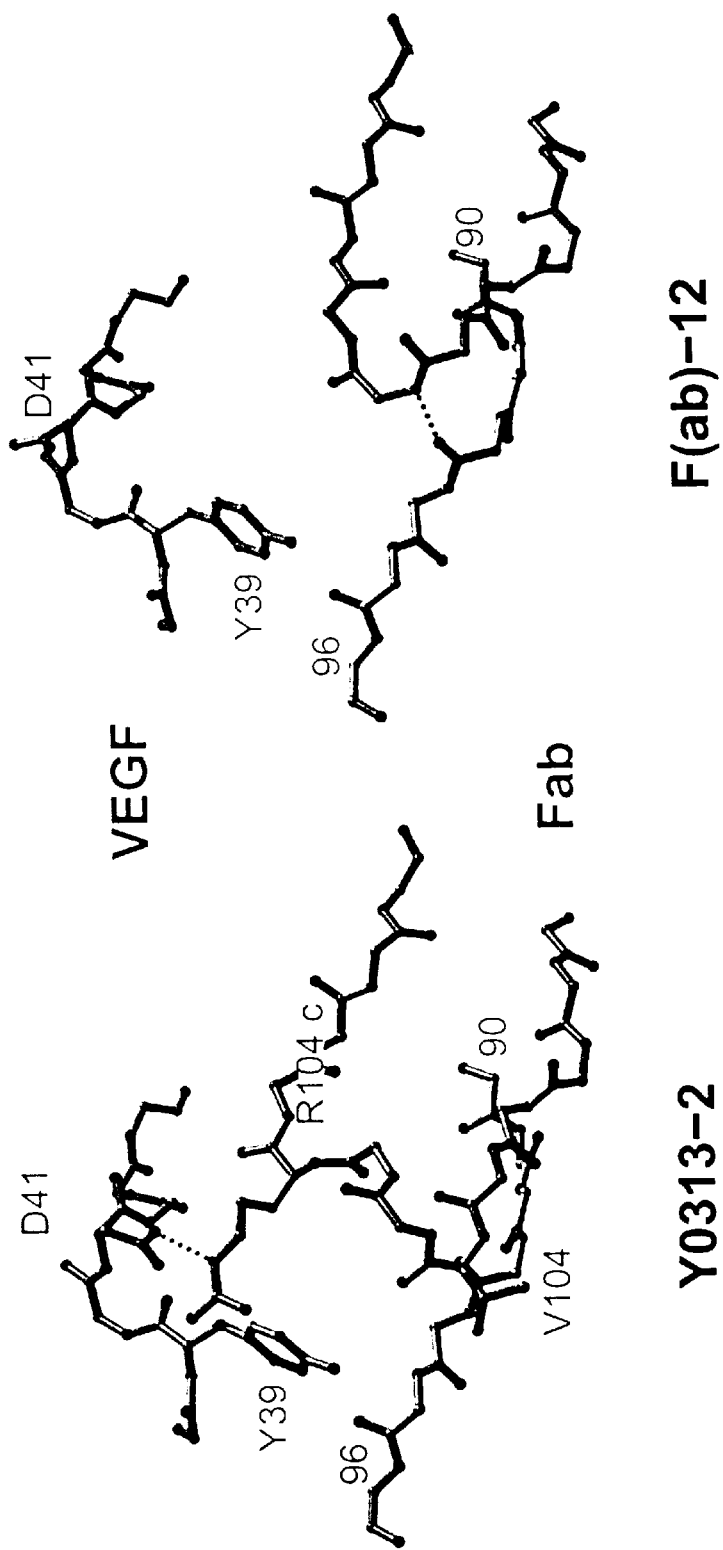
FIG. 5 shows a comparison of portions of the three-dimensional model of F(ab)-12 in complex with VEGF (at right; Muller et al., supra) with a model of Fab Y0313-2 in complex with VEGF (at left) as described herein. In each case, VEGF is shown in yellow, and the respective Fab is shown in green. In the Y0313-2 complex, it can be seen that V104 and R104c make new contacts with VEGF.

Thus, as illustrated in FIGS. 4 and 5, D41 of the VEGF antigen is able to form an ion pair with inserted residue R104c in CDR H3 of variant antibody Y0313-2 of the Example below. FIG. 5 further shows how residue V104 in variant antibody Y0313-2 is able to form a hydrophobic interaction with residues 93 to 95 of the VEGF antigen. Thus, it can be seen that one identifies potential areas where the contacts between antigen and antibody can be improved, so as to increase the affinity of the antibody variant.

Generally one makes changes in hypervariable regions proximal to antigen when the antigen and antibody are complexed together. For example, the hypervariable region of the parent antibody which may be modified as disclosed herein generally has one or more amino acid residues within about 20 Å of one or more amino acid residues of the antigen. The hypervariable region to be altered herein may be one which, in the parent antibody, does not make significant contact with antigen (i.e. a non-contacting hypervariable region can be modified to become a contacting hypervariable region). Preferably however, the hypervariable region to be modified does contact antigen and the method herein serves to increase the contacts between the antigen and the already-contacting hypervariable region.

In another embodiment, one may identify hypervariable region residues which interact with antigen by alanine-scanning mutagenesis of the antigen and/or parent antibody (Muller et al. *Structure* 6(9): 1153–1167 (1998)) or by other means. Hypervariable regions identified as contacting antigen are candidates for amino acid insertion(s) as herein disclosed.

Nucleic acid molecules encoding amino acid sequence variants are prepared by a variety of methods known in the art. These methods include, but are not limited to, oligonucleotide-mediated (or site-directed) mutagenesis, PCR mutagenesis, and cassette mutagenesis of an earlier prepared variant or a non-variant version of the parent antibody. The preferred method for making variants is site directed mutagenesis (see, e.g., Kunkel, *Proc. Natl. Acad. Sci. USA* 82:488 (1985)). Moreover, a nucleic acid sequence can be made synthetically, once the desired amino acid sequence is arrived at conceptually. One can also make the antibody variant by peptide synthesis, peptide ligation or other methods.

Following production of the antibody variant, the activity of that molecule relative to the parent antibody may be determined. As noted above, this may involve determining the binding affinity and/or other biological activities of the antibody. In a preferred embodiment of the invention, a panel of antibody variants are prepared and are screened for binding affinity for the antigen and/or potency in one or more biological activity assays. One or more of the antibody variants selected from an initial screen are optionally subjected to one or more further biological activity assays to confirm that the antibody variant(s) have improved activity in more than one assay.

One preferred method of making and screening insertion mutants involves displaying antibody variants on the surface of filamentous bacteriophage and selecting antibody variants based on their affinity for antigen, by their kinetics of dissociation (off-rate) from antigen, or some other screen for antibody affinity or potency. This was the method used to identify antibody variants with enhanced biological activity in the Example below.

Aside from the above insertions in the hypervariable region of the parent antibody one may make other alterations in the amino acid sequences of one or more of the hypervariable regions. For example, the above amino acid insertions may be combined with deletions or substitutions of other hypervariable region residues. Moreover, one or more alterations (e.g. substitutions) of FR residues may be introduced in the parent antibody where these result in an improvement in the binding affinity of the antibody variant for the antigen. Examples of framework region residues to modify include those which non-covalently bind antigen directly (Amit et al. *Science* 233:747–753 (1986)); interact with/effect the conformation of a CDR (Chothia et al. *J. Mol. Biol.* 196:901–917 (1987)); and/or participate in the $V_L$-$V_H$ interface (EP 239 400B1). Such amino acid sequence alterations may be present in the parent antibody, may be made simulateously with the amino acid insertion(s) herein or may be made after a variant with an amino acid insertion is generated.

The antibody variants may be subjected to other modifications, oftentimes depending on the intended use of the antibody. Such modifications may involve further alteration of the amino acid sequence, fusion to heterologous polypeptide(s) and/or covalent modification. With respect to amino acid sequence alterations, exemplary modifications are elaborated above. For example, any cysteine residue not involved in maintaining the proper conformation of the antibody variant also may be substituted, generally with serine, to improve the oxidative stability of the molecule and prevent aberrant cross linking. Conversely, cysteine bond(s) may be added to the antibody to improve its stability (particularly where the antibody is an antibody fragment such as an Fv fragment). Another type of amino acid variant has an altered glycosylation pattern. This may be achieved by deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X- threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Techniques for producing antibodies, which may be the parent antibody and therefore require modification according to the techniques elaborated herein, follow:

A. Antibody Preparation (i) Antigen Preparation

Soluble antigens or fragments thereof, optionally conjugated to other molecules, can be used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule. Other antigens and forms thereof useful for preparing antibodies will be apparent to those in the art.

(ii) Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 µg or 5 µg of the protein or conjugate (for rabbits or mice, respectively) with 3 volumes of Freund's complete adjuvant and injecting the solution intradermally at multiple sites. One month later the animals are boosted with 1/5 to 1/10 the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(iii) Monoclonal Antibodies

Monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp.59–103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51–63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp.59–103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce immunoglobulin protein, to obtain the synthesis of monoclonal antibodies in the recombinant host cells. Recombinant production of antibodies will be described in more detail below.

In a further embodiment, antibodies or antibody fragments can be isolated from antibody phage libraries generated using the techniques described in McCafferty et al., *Nature*, 348:552–554 (1990). Clackson et al., *Nature*, 352:624–628 (1991) and Marks et al., *J. Mol. Biol.*, 222:581–597 (1991) describe the isolation of murine and human antibodies, respectively, using phage libraries. Subsequent publications describe the production of high affinity (nM range) human antibodies by chain shuffling (Marks et al., *Bio/Technology*, 10:779–783 (1992)), as well as combinatorial infection and in vivo recombination as a strategy for constructing very large phage libraries (Waterhouse et al., *Nuc. Acids. Res.*, 21:2265–2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., *Proc. Natl Acad. Sci. USA*, 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

(iv) Humanized and Human Antibodies

A humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522–525 (1986); Riechmann et al., *Nature*, 332:323–327 (1988); Verhoeyen et al., Science, 239:1534–1536 (1988)), by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable domain sequences. The human sequence which is closest to that of the rodent is then accepted as the human FR for the humanized antibody (Sims et al., *J. Immunol.*, 151:2296 (1993); Chothia et al., *J. Mol. Biol.*, 196:901 (1987)). Another method uses a particular FR derived from the consensus sequence of all human antibodies of a particular subgroup of light or heavy chains. The same FR may be used for several different humanized antibodies (Carter et al., *Proc. Natl. Acad. Sci. USA*, 89:4285 (1992); Presta et al., *J. Immnol.*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255–258 (1993); Bruggermann et al., *Year in Immuno.*, 7:33 (1993); and Duchosal et al. Nature 355:258 (1992). Human antibodies can also be derived from phage-display libraries (Hoogenboom et al., *J. Mol. Biol.*, 227:381 (1991); Marks et al., *J. Mol. Biol.*, 222:581–597 (1991); Vaughan et al. *Nature Biotech* 14:309 (1996)).

(v) Antibody Fragments

Various techniques have been developed for the production of antibody fragments. Traditionally, these fragments were derived via proteolytic digestion of intact antibodies (see, e.g., Morimoto et al., *Journal of Biochemical and Biophysical Methods* 24:107–117 (1992) and Brennan et al., *Science*, 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., Bio/Technology 10:163–167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185.

(vi) Multispecific Antibodies

Multispecific antibodies have binding specificities for at least two different antigens. While such molecules normally will only bind two antigens (i.e. bispecific antibodies, BsAbs), antibodies with additional specificities such as trispecific antibodies are encompassed by this expression when used herein. Examples of BsAbs include those with one arm directed against a tumor cell antigen and the other arm directed against a cytotoxic trigger molecule such as anti-FcγRI/anti-CD15, anti-p185$^{HER2}$/FcγRIII (CD16), anti-CD3/anti-malignant B-cell (1D10), anti-CD3/anti-p185$^{HER2}$, anti-CD3/anti-p97, anti-CD3/anti-renal cell carcinoma, anti-CD3/anti-OVCAR-3, anti-CD3/L-D1 (anti-colon carcinoma), anti-CD3/anti-melanocyte stimulating hormone analog, anti-EGF receptor/anti-CD3, anti-CD3/anti-CAMA1, anti-CD3/anti-CD19, anti-CD3/MoV18, anti-neural cell ahesion molecule (NCAM)/anti-CD3, anti-folate binding protein (FBP)/anti-CD3, anti-pan carcinoma associated antigen (AMOC-31)/anti-CD3; BsAbs with one arm which binds specifically to a tumor antigen and one arm which binds to a toxin such as anti-saporin/anti-Id-1, anti-CD22/anti-saporin, anti-CD7/anti-saporin, anti-CD38/anti-saporin, anti-CEA/anti-ricin A chain, anti-CEA/anti-vinca alkaloid; BsAbs for converting enzyme activated prodrugs such as anti-CD30/anti-alkaline phosphatase (which catalyzes conversion of mitomycin phosphate prodrug to mitomycin alcohol); BsAbs which can be used as fibrinolytic agents such as anti-fibrin/anti-tissue plasminogen activator (tPA), anti-fibrin/anti-urokinase-type plasminogen activator (uPA); BsAbs for targeting immune complexes to cell surface receptors such as anti-low density lipoprotein (LDL)/anti-Fc receptor (e.g. FcγRI, FcγRII or FcγRIII); BsAbs for use in therapy of infectious diseases such as anti-CD3/anti-herpes simplex virus (HSV), anti-T-cell receptor:CD3 complex/anti-influenza, anti-FcγR/anti-HIV; BsAbs for tumor detection in vitro or in vivo such as anti-CEA/anti-EOTUBE, anti-CEA/anti-DPTA, anti-p185$^{HER2}$/anti-hapten; BsAbs as vaccine adjuvants; and BsAbs as diagnostic tools such as anti-rabbit IgG/anti-ferritin, anti-horse radish peroxidase (HRP)/anti-hormone, anti-somatostatin/anti-substance P, anti-HRP/anti-FITC. Examples of trispecific antibodies include anti-CD3/anti-CD4/anti-CD37, anti-CD3/anti-CD5/anti-CD37 and anti-CD3/anti-CD8/anti-CD37. Bispecific antibodies can be prepared as full length antibodies or antibody fragments (e.g. F(ab')$_2$ bispecific antibodies).

Methods for making bispecific antibodies are known in the art. Traditional production of full length bispecific antibodies is based on the coexpression of two immunoglobulin heavy chain-light chain pairs, where the two chains have different specificities (Millstein et al., *Nature*, 305:537–539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655–3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach described in WO96/27011, the interface between a pair of antibody molecules can be engineered to maximize the percentage of heterodimers which are recovered from recombinant cell culture. The preferred interface comprises at least a part of the C$_H$3 domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217–225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al.,*J. Immunol.*, 148(5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444–6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147: 60 (1991).

(vii) Effector Function Engineering

It may be desirable to modify the antibody of the invention with respect to effector function, so as to enhance the effectiveness of the antibody in treating cancer, for example. For example cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al.,*J. Exp Med.* 176:1191–1195 (1992) and Shopes, B. *J. Immunol.* 148:2918–2922 (1992). Homodimeric antibodies with enhanced anti-tumor activity may also be prepared using heterobifunctional cross-linkers as described in Wolff et al. Cancer Research 53:2560–2565 (1993). Alternatively, an antibody can be engineered which has dual Fc regions and may thereby have enhanced complement lysis and ADCC capabilities. See Stevenson et al. *Anti-Cancer Drug Design* 3:219–230 (1989).

(viii) Immunoconjugates

The invention also pertains to immunoconjugates comprising the antibody described herein conjugated to a cytotoxic agent such as a chemotherapeutic agent, toxin (e.g. an enzymatically active toxin of bacterial, fungal, plant or animal origin, or fragments thereof), or a radioactive isotope (i.e., a radioconjugate).

Chemotherapeutic agents useful in the generation of such immunoconjugates have been described above. Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. A variety of radionuclides are available for the production of radioconjugate antibodies. Examples include $^{212}$Bi, $^{133}$I, $^{131}$In, $^{90}$Y and $^{186}$Re.

Conjugates of the antibody and cytotoxic agent are made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

(ix) Immunoliposomes

The antibody variants disclosed herein may also be formulated as immunoliposomes. Liposomes containing the antibody are prepared by methods known in the art, such as described in Epstein et al., *Proc. Natl. Acad. Sci. USA*, 82:3688 (1985); Hwang et al., *Proc. Natl Acad. Sci. USA*, 77:4030 (1980); and U.S. Pat. Nos. 4,485,045 and 4,544, 545. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al. *J. Biol. Chem.* 257: 286–288 (1982) via a disulfide interchange reaction. A chemotherapeutic agent (such as Doxorubicin) is optionally contained within the liposome. See Gabizon et al. *J. National Cancer Inst.*81(19)1484 (1989)

(x) Antibody Dependent Enzyme Mediated Prodrug Therapy (ADEPT)

The antibody of the present invention may also be used in ADEPT by conjugating the antibody to a prodrug-activating enzyme which converts a prodrug (e.g. a peptidyl chemotherapeutic agent, see WO81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as beta-galactosidase and neuraminidase useful for converting glycosylated prodrugs into free drugs; beta-lactamase useful for converting drugs derivatized with beta-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, Nature 328: 457–458 (1987)). Antibody-abzyme conjugates can be prepared as described herein for delivery of the abzyme to a tumor cell population.

The enzymes of this invention can be covalently bound to the antibody variant by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., Nature, 312: 604–608 (1984)).

(xi) Antibody-salvage Receptor Binding Epitope Fusions.

In certain embodiments of the invention, it may be desirable to use an antibody fragment, rather than an intact antibody, to increase tumor penetration, for example. In this case, it may be desirable to modify the antibody fragment in order to increase its serum half life. This may be achieved, for example, by incorporation of a salvage receptor binding epitope into the antibody fragment (e.g. by mutation of the appropriate region in the antibody fragment or by incorporating the epitope into a peptide tag that is then fused to the antibody fragment at either end or in the middle, e.g., by DNA or peptide synthesis).

The salvage receptor binding epitope preferably constitutes a region wherein any one or more amino acid residues from one or two loops of a Fc domain are transferred to an analogous position of the antibody fragment. Even more preferably, three or more residues from one or two loops of the Fc domain are transferred. Still more preferred, the epitope is taken from the CH2 domain of the Fc region (e.g., of an IgG) and transferred to the CH1, CH3, or $V_H$ region, or more than one such region, of the antibody. Alternatively, the epitope is taken from the CH2 domain of the Fc region and transferred to the $C_L$ region or $V_L$ region, or both, of the antibody fragment. See, e.g., U.S. Pat. 5,739,277, issued Apr. 14, 1998.

(xii) Covalent Modifications

Covalent modifications of the antibody are included within the scope of this invention. They may be made by chemical synthesis or by enzymatic or chemical cleavage of the antibody, if applicable. Other types of covalent modifications of the antibody are introduced into the molecule by reacting targeted amino acid residues of the antibody with an organic derivatizing agent that is capable of reacting with selected side chains or the N- or C-terminal residues.

Removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Hakimuddin, et al. Arch. Biochem. Biophys. 259:52 (1987) and by Edge et al. Anal. Biochem., 118:131 (1981). Enzymatic cleavage of carbohydrate moieties on antibodies can be achieved by the use of a variety of endo- and exo-glycosidases as described by Thotakura et al. Meth. Enzymol. 138:350 (1987).

Another type of covalent modification of the antibody comprises linking the antibody to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

B. Vectors, Host Cells and Recombinant Methods

The invention also provides isolated nucleic acid encoding an antibody variant as disclosed herein, vectors and host cells comprising the nucleic acid, and recombinant techniques for the production of the antibody variant.

For recombinant production of the antibody variant, the nucleic acid encoding it is isolated and inserted into a replicable vector for further cloning (amplification of the DNA) or for expression. DNA encoding the monoclonal antibody variant is readily isolated and sequenced using conventional procedures (e.g., by using oligonucleotide probes that are capable of binding specifically to genes encoding the heavy and light chains of the antibody variant). Many vectors are available. The vector components generally include, but are not limited to, one or more of the following: a signal sequence, an origin of replication, one or more marker genes, an enhancer element, a promoter, and a transcription termination sequence.

(i) Signal Sequence Component

The antibody variant of this invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process the native antibody signal sequence, the signal sequence is substituted by a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase leader, α factor leader (including Saccharomyces and Kluyveromyces α-factor leaders), or acid phosphatase leader, the C. albicans glucoamylase leader, or the signal described in WO 90/13646. In mammalian cell expression, mammalian signal sequences as well as viral secretory leaders, for example, the herpes simplex gD signal, are available.

The DNA for such precursor region is ligated in reading frame to DNA encoding the antibody variant.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2 μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity.

Alternatively, host cells (particularly wild-type hosts that contain endogenous DHFR) transformed or co-transformed with DNA sequences encoding antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature*, 282:39 (1979)). The trp1 gene provides a selection marker for a mutant strain of yeast lacking the ability to grow in tryptophan, for example, ATCC No. 44076 or PEP4-1. Jones, *Genetics*, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 um circular plasmid pKD1 can be used for transformation of Kluyveromyces yeasts. Alternatively, an expression system for large-scale production of recombinant calf chymosin was reported for *K. lactis*. Van den Berg, *Bio/Technology*, 8:135 (1990). Stable multi-copy expression vectors for secretion of mature recombinant human serum albumin by industrial strains of Kluyveromyces have also been disclosed. Fleer et al., *Bio/Technology*, 9:968–975 (1991).

(iv) Promoter component

Expression and cloning vectors usually contain a promoter that is recognized by the host organism and is operably linked to the antibody nucleic acid. Promoters suitable for use with prokaryotic hosts include the phoA promoter , beta-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phospho-fructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. Alternatively, the rous sarcoma virus long terminal repeat can be used as the promoter.

(v) Enhancer Element Component

Transcription of a DNA encoding the antibody of this invention by higher eukaryotes is often increased by inserting an enhancer sequence into the vector. Many enhancer sequences are now known from mammalian genes (globin, elastase, albumin, alpha-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. See also Yaniv, *Nature* 297:17–18 (1982) on enhancing elements for activation of eukaryotic promoters. The enhancer may be spliced into the vector at a position 5' or 3' to the antibody-encoding sequence, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the antibody. One useful transcription termination component is the bovine growth hormone polyadenylation region. See WO94/11026 and the expression vector disclosed therein.

(vii) Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as Escherichia, e.g., *E. coli*, Enterobacter, Erwinia, Klebsiella, Proteus, Salmonella, e.g., *Salmonella typhimurium*, Serratia, e.g., *Serratia marcescans*, and Shigella, as well as Bacilli such as *B. subtilis* and *B. licheniformis* (e.g., *B. licheniformis* 41P disclosed in DD 266,710 published Apr. 12, 1989), Pseudomonas such as *P. aeruginosa*, and Streptomyces. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; Kluyveromyces hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K . drosophilarum* (ATCC 36,906), *K . thermotolerans*, and *K. marxianus; yarrowia* (EP 402,226); *Pichia pastoris* (EP 183,070); Candida; *Trichoderma reesia* (EP 244,234); *Neurospora crassa*; Schwanniomyces such as *Schwanniomyces occidentalis*; and filamentous fungi such as, e.g., Neurospora, Penicillium, Tolypocladium, and Aspergillus hosts such as *A. nidulans* and *A. niger*.

Suitable host cells for the expression of glycosylated antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980)); mouse sertoli cells (TM4, Mather, *Biol. Reprod.* 23:243–251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al. , *Annals N.Y. Acad. Sci.* 383:44–68 (1982)); MRC 5 cells; FS4 cells; and a human hepatoma line (Hep G2).

Host cells are transformed with the above-described expression or cloning vectors for antibody production and cultured in conventional nutrient media modified as appropriate for inducing promoters, selecting transformants, or amplifying the genes encoding the desired sequences.

(viii) Culturing the Host Cells

The host cells used to produce the antibody variant of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(ix) Antibody Purification

When using recombinant techniques, the antibody variant can be produced intracellularly, in the periplasmic space, or directly secreted into the medium. If the antibody variant is produced intracellularly, as a first step, the particulate debris, either host cells or lysed fragments, is removed, for example, by centrifugation or ultrafiltration. Carter et al., *Bio/Technology* 10:163–167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody variant is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody variant. Protein A can be used to purify antibodies that are based on human γ1, γ2, or γ4 heavy chains (Lindmark et al., *J. Immunol. Meth.* 62:1–13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody variant comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody variant to be recovered.

C. Pharmaceutical Formulations

Therapeutic formulations of the antibody variant are prepared for storage by mixing the antibody variant having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. For example, it may be desirable to further provide an immunosuppressive agent. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody variant, which matrices are in the form of shaped articles, e.g., films, or microcapsule. Examples of sustained-release matrices include polyesters, hydrogels (for example, poly(2-hydroxyethyl-methacrylate), or poly (vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S-S bond formation through thio-disulfide interchange, stabilization may be achieved by modifying sulfhydryl residues, lyophilizing from acidic solutions, controlling moisture content, using appropriate additives, and developing specific polymer matrix compositions.

D. Non-Therapeutic Uses for the Antibody Variant

The antibody variants of the invention may be used as affinity purification agents. In this process, the antibodies are immobilized on a solid phase such a Sephadex resin or filter paper, using methods well known in the art. The immobilized antibody variant is contacted with a sample containing the antigen to be purified, and thereafter the support is washed with a suitable solvent that will remove substantially all the material in the sample except the antigen to be purified, which is bound to the immobilized antibody variant. Finally, the support is washed with another suitable solvent, such as glycine buffer, pH 5.0, that will release the antigen from the antibody variant.

The variant antibodies may also be useful in diagnostic assays, e.g., for detecting expression of an antigen of interest in specific cells, tissues, or serum.

For diagnostic applications, the antibody variant typically will be labeled with a detectable moiety. Numerous labels are available which can be generally grouped into the following categories:

(a) Radioisotopes, such as $^{35}S$, $^{14}C$, $^{125}I$, $^{3}H$, and $^{131}I$. The antibody variant can be labeled with the radioisotope using the techniques described in *Current Protocols in Immunology*, Volumes 1 and 2, Coligen et al., Ed. Wiley-Interscience, New York, N.Y., Pubs. (1991) for example and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the antibody variant using the techniques disclosed in *Current Protocols in Immunology*, supra, for example. Fluorescence can be quantified using a fluorimeter.

(c) Various enzyme-substrate labels are available and U.S. Pat. No. 4,275,149 provides a review of some of these. The enzyme generally catalyzes a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, beta-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in *Methods in Enzym.* (ed J. Langone & H. Van Vunakis), Academic press, New York, 73:147–166 (1981).

Examples of enzyme-substrate combinations include, for example:

(i) Horseradish peroxidase (HRPO) with hydrogen peroxidase as a substrate, wherein the hydrogen peroxidase oxidizes a dye precursor (e.g.,orthophenylene diamine (OPD) or 3,3',5,5'-tetramethyl benzidine hydrochloride (TMB));

(ii) alkaline phosphatase (AP) with para-Nitrophenyl phosphate as chromogenic substrate; and (iii) beta-D-galactosidase (beta-D-Gal) with a chromogenic substrate (e.g., p-nitrophenyl-beta-D-galactosidase) or fluorogenic substrate 4-methylumbelliferyl-beta-D-galactosidase.

Numerous other enzyme-substrate combinations are available to those skilled in the art. For a general review of these, see U.S. Pat. Nos. 4,275,149 and 4,318,980.

Sometimes, the label is indirectly conjugated with the antibody variant. The skilled artisan will be aware of various techniques for achieving this. For example, the antibody variant can be conjugated with biotin and any of the three broad categories of labels mentioned above can be conjugated with avidin, or vice versa. Biotin binds selectively to avidin and thus, the label can be conjugated with the antibody variant in this indirect manner. Alternatively, to achieve indirect conjugation of the label with the antibody variant, the antibody variant is conjugated with a small hapten (e.g., digoxin) and one of the different types of labels mentioned above is conjugated with an anti-hapten antibody variant (e.g., anti-digoxin antibody). Thus, indirect conjugation of the label with the antibody variant can be achieved.

In another embodiment of the invention, the antibody variant need not be labeled, and the presence thereof can be detected using a labeled antibody which binds to the antibody variant.

The antibodies of the present invention may be employed in any known assay method, such as competitive binding assays, direct and indirect sandwich assays, and immunoprecipitation assays. Zola, *Monoclonal Antibodies: A Manual of Techniques*, pp.147–158 (CRC Press, Inc. 1987).

Competitive binding assays rely on the ability of a labeled standard to compete with the test sample analyze for binding with a limited amount of antibody variant. The amount of antigen in the test sample is inversely proportional to the amount of standard that becomes bound to the antibodies. To facilitate determining the amount of standard that becomes bound, the antibodies generally are insolubilized before or after the competition, so that the standard and analyze that are bound to the antibodies may conveniently be separated from the standard and analyze which remain unbound.

Sandwich assays involve the use of two antibodies, each capable of binding to a different immunogenic portion, or epitope, of the protein to be detected. In a sandwich assay, the test sample analyze is bound by a first antibody which is immobilized on a solid support, and thereafter a second antibody binds to the analyze, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

For immunohistochemistry, the tumor sample may be fresh or frozen or may be embedded in paraffin and fixed with a preservative such as formalin, for example.

The antibodies may also be used for in vivo diagnostic assays. Generally, the antibody variant is labeled with a radionuclide (such as $^{111}$In, $^{99}$Tc, $^{14}$C, $^{131}$I, $^{125}$I, $^{3}$H, $^{32}$P or $^{35}$S) so that the tumor can be localized using immunoscintiography.

E. Diagnostic Kits

As a matter of convenience, the antibody variant of the present invention can be provided in a kit, i.e., a packaged combination of reagents in predetermined amounts with instructions for performing the diagnostic assay. Where the antibody variant is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

F. In Vivo Uses for the Antibody Variant

For therapeutic applications, the antibody variants of the invention are administered to a mammal, preferably a human, in a pharmaceutically acceptable dosage form such as those discussed above, including those that may be administered to a human intravenously as a bolus or by continuous infusion over a period of time, by intramuscular, intraperitoneal, intra-cerebrospinal, subcutaneous, intra-articular, intrasynovial, intrathecal, oral, topical, or inhalation routes. The antibodies also are suitably administered by intra-tumoral, peri-tumoral, intra-lesional, or peri-lesional routes, to exert local as well as systemic therapeutic effects. The intra-peritoneal route is expected to be particularly useful, for example, in the treatment of ovarian tumors. In addition, the antibody variant is suitably administered by pulse infusion, particularly with declining doses of the antibody variant. Preferably the dosing is given by injections, most preferably intravenous or subcutaneous injections, depending in part on whether the administration is brief or chronic.

For the prevention or treatment of disease, the appropriate dosage of antibody variant will depend on the type of disease to be treated, the severity and course of the disease, whether the antibody variant is administered for preventive or therapeutic purposes, previous therapy, the patient's clinical history and response to the antibody variant, and the discretion of the attending physician. The antibody variant is suitably administered to the patient at one time or over a series of treatments.

The example herein concerns an anti-VEGF antibody. Anti-VEGF antibodies are useful in the treatment of various neoplastic and non-neoplastic diseases and disorders. Neoplasms and related conditions that are amenable to treatment include breast carcinomas, lung carcinomas, gastric carcinomas, esophageal carcinomas, colorectal carcinomas, liver carcinomas, ovarian carcinomas, thecomas, arrhenoblastomas, cervical carcinomas, endometrial carcinoma, endometrial hyperplasia, endometriosis, fibrosarcomas, choriocarcinoma, head and neck cancer, nasopharyngeal carcinoma, laryngeal carcinomas, hepatoblastoma, Kaposi's sarcoma, melanoma, skin carcinomas, hemangioma, cavernous hemangioma, hemangioblastoma, pancreas carcinomas, retinoblastoma, astrocytoma, glioblastoma, Schwannoma, oligodendroglioma, medulloblastoma, neuroblastomas, rhabdomyosarcoma, osteogenic sarcoma, leiomyosarcomas, urinary tract carcinomas, thyroid carcinomas, Wilm's tumor, renal cell carcinoma, prostate carcinoma, abnormal vascular proliferation associated with phakomatoses, edema (such as that associated with brain tumors), and Meigs' syndrome.

Non-neoplastic conditions that are amenable to treatment include rheumatoid arthritis, psoriasis, atherosclerosis, diabetic and other proliferative retinopathies including retinopathy of prematurity, retrolental fibroplasia, neovascular glaucoma, age-related macular degeneration, thyroid hyperplasias (including Grave's disease), corneal and other tissue transplantation, chronic inflammation, lung inflammation, nephrotic syndrome, preeclampsia, ascites, pericardial effusion (such as that associated with pericarditis), and pleural effusion.

Age-related macular degeneration (AMD) is a leading cause of severe visual loss in the elderly population. The exudative form of AMD is characterized by choroidal neovascularization and retinal pigment epithelial cell detachment. Because choroidal neovascularization is associated with a dramatic worsening in prognosis, the VEGF antibodies of the present invention are expected to be especially useful in reducing the severity of AMD.

Depending on the type and severity of the disease, about 1 μg/kg to 15 mg/kg (e.g., 0.1–20 mg/kg) of antibody variant is an initial candidate dosage for administration to the patient, whether, for example, by one or more separate administrations, or by continuous infusion. A typical daily dosage might range from about 1 μg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

The antibody variant composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody variant to be administered will be governed by such considerations, and is the minimum amount necessary to prevent, ameliorate, or treat a disease or disorder. The antibody variant need not be, but is optionally formulated with one or more agents currently used to prevent or treat the disorder in question. The effective amount of such other agents depends on the amount of antibody variant present in the formulation, the type of disorder or treatment, and other factors discussed above. These are generally used in the same dosages and with administration routes as used hereinbefore or about from 1 to 99% of the heretofore employed dosages.

G. Articles of Manufacture

In another embodiment of the invention, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is the antibody variant. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

EXAMPLE 1

In this example, antibody variants containing randomized peptide inserts within the antibody CDRs are prepared by phage display which substantially improve the affinity of a humanized Fab for VEGF. Crystallography suggests that these changes result in an increased contact area with antigen.

VEGF:Fab X-ray Co-Crystal Structure: A crystal structure of the complex between the VEGF antigen and anti-VEGF parent antibody was prepared as described in Muller et al., *Structure* 6(9):1153–1167 (1998). The conclusion that the three VH CDRs are the main determinants of Fab binding to VEGF is supported by the high-resolution crystal structure of the VEGF:Fab (v36) complex. In addition, the major energetic determinants largely coincide with the principal contacting residues of the Fab in the complex.

Several randomized libraries were designed with a peptide insertion placed in the antigen-contacting CDRs which, from the crystal structure, were expected to increase the potential contact between the antibody and the antigen.

Design of CDR Random Loop-Insertion Libraries: Based upon inspection of the VEGF:Fab crystal structure, it was postulated that additional contacts, contributing additional binding energy between the Fab and VEGF, could be generated through the addition of peptide inserts within one or more CDRs of the Fab. Because the nature and relative contributions of such additional interactions would be difficult to predict, randomized loop sequences (Xn) were directly inserted into each of the four CDRs proximal to the existing VEGF binding site using NNS codons, and a frameshifted Fab vector as template. The length of loop was chosen based upon distances in the crystal structure between exit/entry points of the loop on the hypervariable region and possible interaction sites on the surface of VEGF. In addition, one or more residues within each loop were deleted in some of these templates, as judged necessary to accommodate the new peptide loop.

Three such loops were designed for VH1, including insertions of 4, 5, or 6 residues between Y27 and T28. In VH2, two inserted peptides of 3 or 4 residues were placed between Y54 and T55. Also in VH2, a 6-residue random peptide was used to replace residues T55 and H56. In VH3, a 4-residue or 5-residue peptide was used to replace G104, and a 5-residue or 6-residue peptide was used to replace residues G104 and S105. Finally, in VL3, a random peptide of either 4 or 6 residues was inserted between S92 and T93.

Second-Generation Selections of anti-VEGF Libraries: Templates for random mutagenesis were constructed starting from the Fab-g3 phagemid pY0192 (WO98/45331) and frameshift oligonucleotides (which prevent expression of a functional template Fab): YC-82, YC-85, YC-89, YC-92, YC-94, and YC-97 (Table 1).

The resulting transformants yielded libraries with complexities ranging from $6 \times 10^7$ to $5 \times 10^8$ suggesting that the libraries were comprehensive in covering all possible variants.

Each library was sorted separately for the first round; thereafter, libraries with the same site of insertion were combined 10 and sorted together as one. Therefore, library YC-83 was combined with library YC-84; library YC-86 with libraries YC-87 and YC-88; library YC-90 with YC-91;

TABLE 1

Frameshift oligos for CDR-insert template mutagenesis

| Oligo # | Region | Sequence | SEQ. ID NO: |
|---|---|---|---|
| YC-82 | VL3 | C TGT CAA CAG TAT AGC T ACC GTG CCG TGG ACG | SEQ. ID NO:1 |
| YC-85 | VH1 | GCA GCT TCT GGC TAT G ACC TTC ACC AAC TAT G | SEQ. ID NO:2 |
| YC-89 | VH2 | GA TGG ATT AAC ACC TAT G ACC GGT GAA CCG ACC | SEQ. ID NO:3 |
| YC-92 | VH2 | GA TGG ATT AAC ACC TAT T GAA CCG ACC TAT GCT | SEQ. ID NO:4 |
| YC-94 | VH3 | G TAC CCG CAC TAT TAT G AGC AGC CAC TGG TAT | SEQ. ID NO:5 |
| YC-97 | VH3 | G TAC CCG CAC TAT TAT G AGC CAC TGG TAT TTC | SEQ. ID NO:6 |

The corresponding randomization oligonucleotides (which employ NNS at the sites targeted for randomization) were YC-83, YC-84 in VL3; YC-86, YC-87, YC-88 in VH1; YC-90, YC91 and YC-93 in VH2; and YC-95, YC-96, YC-98, YC-99 in VH3. See Table 2 below.

library YC-95 with YC-96; and library YC-98 with YC-99. These libraries were sorted essentially as described in WO98/45331, except the incubation with PBS/TWEEN 20® buffer after phage binding was carried out as described in Table 3.

TABLE 2

Random oligos for CDR-insert library constructions

| Oligo # | Region | (Comments) | Sequence | SEQ ID NO: |
|---|---|---|---|---|
| YC-83 | VL3 | (insert 4 residues) | C TGT CAA CAG TAT AGC NNS NNS NNS NNS ACC GTG CCG TGG ACG | SEQ. ID NO:7 |
| YC-84 | VL3 | (insert 6 residues) | C TGT CAA CAG TAT AGC NNS NNS NNS NNS NNS NNS ACC GTG CCG TGG ACG | SEQ. ID NO:8 |
| YC-86 | VH1 | (insert 4 residues) | GCA GCT TCT GGC TAT NNS NNS NNS NNS ACC TTC ACC AAC TAT G | SEQ. ID NO:9 |
| YC-87 | VH1 | (insert 5 residues) | GCA GCT TCT GGC TAT NNS NNS NNS NNS NNS ACC TTC ACC AAC TAT G | SEQ. ID NO:10 |
| YC-88 | VH1 | (insert 6 residues) | GCA GCT TCT GGC TAT NNS NNS NNS NNS NNS NNS ACC TTC ACC AAC TAT G | SEQ. ID NO:11 |
| YC-90 | VH2 | (insert 3 residues) | GA TGG ATT AAC ACC TAT NNS NNS NNS ACC GGT GAA CCG ACC | SEQ. ID NO:12 |
| YC-91 | VH2 | (insert 4 residues) | GA TGG ATT AAC ACC TAT NNS NNS NNS NNS ACC GGT GAA CCG ACC | SEQ. ID NO:13 |
| YC-93 | VH2 | (insert 6 residues) | GA TGG ATT AAC ACC TAT NNS NNS NNS NNS NNS NNS GAA CCG ACC TAT GCT G | SEQ. ID NO:14 |
| YC-95 | VH3 | (insert 4 residues) | G TAC CCG CAC TAT TAT NNS NNS NNS NNS AGC AGC CAC TGG TAT TTC | SEQ. ID NO:15 |
| YC-96 | VH3 | (insert 5 residues) | G TAC CCG CAC TAT TAT NNS NNS NNS NNS NNS AGC AGC CAC TGG TAT TTC | SEQ. ID NO:16 |
| YC-98 | VH3 | (insert 5 residues) | G TAC CCG CAC TAT TAT NNS NNS NNS NNS NNS AGC CAC TGG TAT TTC | SEQ. ID NO:17 |
| YC-99 | VH3 | (insert 6 residues) | G TAC CCG CAC TAT TAT NNS NNS NNS NNS NNS NNS AGC CAC TGG TAT TTC | SEQ. ID NO:18 |

TABLE 3

Conditions for secondary selections of Fab variants

| round of selection | incubation time (hr) | incubation solution | incubation temp. (° C.) |
|---|---|---|---|
| 1 | 0 | 0 | room temp. |
| 2 | 1 | ELISA buffer | room temp. |
| 3 | 2 | 1 μM VEGF/ELISA | room temp. |
| 4 | 18 | 1 μM VEGF/ELISA | room temp. |
| 5 | 37 | 1 μM VEGF/ELISA | room temp. |
| 6 | 17 hr @ R.T./30 h @ 37° C. | same as above | room temp./ 37° C. |
| 7 | 63 | same as above | 37° C. |
| 8 | 121 | same as above | 37° C. |

ELISA buffer contained 0.5% bovine serum albumin and 0.05% TWEEN 20® in PBS. VEGF was included in the incubation buffer to minimize rebinding of phage to VEGF coated on the surface of the plate.

Sorting of some of these libraries yielded VEGF-binding phage enrichments over 5 to 8 rounds of selection. After five to eight rounds of selections, ten to twenty clones from each library were isolated from carbenicillin containing plates harboring E. coli (XL1) colonies which had been infected with an eluted phage pool. Colonies were isolated and grown with helper phage to obtain single-stranded DNA for sequencing. Clones were picked from those libraries that enriched for DNA sequencing. The results are shown table 4. Libraries showing no enrichment were not sequenced.

TABLE 4

Summary of CDR Insertion Libraries

| Oligos | | | Site of | No. of added residues | |
|---|---|---|---|---|---|
| Stop oligo | Insert oligo | CDR | Insertion | Net | Total |
| YC-85 | YC-86 | H1 | Y27^T28 | 4 | 4 |
| YC-85 | YC-87 | H1 | Y27^T28 | 5 | 5 |
| YC-85 | YC-88 | H1 | Y27^T28 | 6 | 6 |
| YC-89 | YC-90 | H2 | Y54^T55 | 3 | 3 |
| YC-89 | YC-91 | H2 | Y54^T55 | 4 | 4 |
| YC-92 | YC-93 | H2 | Y54^E57 | 4 | 6 |
| YC-94 | YC-95 | H3 | Y103^S105 | 3 | 4 |
| YC-94 | YC-96 | H3 | Y103^S105 | 4 | 5 |
| YC-97 | YC-98 | H3 | Y103^S106 | 3 | 5 |
| YC-97 | YC-99 | H3 | Y103^S106 | 4 | 6 |
| YC-82 | YC-83 | L3 | S92^T93 | 4 | 4 |
| YC-82 | YC-84 | L3 | S92^T93 | 6 | 6 |

For VH1, only library YC-86 showed enrichment. Sequencing revealed that, although a 4-residue insert was designed in this library, all of the sequenced clones contained no net insertion, but instead point mutations at T28 and F29. This suggests that this antibody is relatively intolerant of insertions in this hypervariable region.

A similar result was seen for the VH2 libraries, where only library YC-90 showed enrichment. Again, clones found were either wild-type (Y0192) or a point mutant, Y54W. This suggests that this antibody is also relatively intolerant of insertions in the VH2 CDR.

Again, a similar result was obtained for the VL3 libraries. In this case, only library YC-83 showed enrichment, and the selected clones had point mutations at T93 and/or V94, rather than the designed insertion. This suggests that this antibody is also relatively intolerant of insertions in the VL3 CDR.

In contrast, two VH3 libraries showed enrichment: YC-95 and YC-98. Moreover, sequencing of selected clones showed that the Fab variants indeed contained insertion sequences.

Amino acid sequences of anti-VEGF variants from the various libraries are shown in Tables 5–15 below. The sequence of the randomized region only is shown as deduced from DNA sequencing. Sites where randomized inserted sequences were made are shown in bold. An asterisk denotes a contaminating phagemid from another library.

TABLE 5

Protein sequences of anti-VEGF variants from library YC-86
Round 7 (VEGF eluted phage)

| Name | VH1 sequence (residues 26–35) | SEQ ID NO: | (# clones/10) |
|---|---|---|---|
| Y0241-1 | GYDFTNYGIN | SEQ. ID NO:19 | 4 |
| Y0241-6 | GYDTTNYGIN | SEQ. ID NO:20 | 3 |
| Y0241-7 | GYDWTNYGIN | SEQ. ID NO:21 | 3 |

TABLE 6

Protein sequences of anti-VEGF variants from library YC-90
Round 7 (VEGF eluted phage)

| Name | VH2 sequence (residues 50–62) | SEQ ID NO: | (# clones/10) |
|---|---|---|---|
| Y0242-1 | WINTWTGEPTYAA | SEQ. ID NO:22 | 4 |
| *Y0192 | | | 6 |

TABLE 7

Protein sequences of anti-VEGF variants from library YC-83
Round 7 (VEGF eluted phage)

| Name | VL3 sequence (residues 89–97) | SEQ ID NO: | (# clones/9) |
|---|---|---|---|
| Y0241-2 | QQYSATPWT | SEQ. ID NO:23 | 1 |
| Y0241-3 | QQYSNVPWT | SEQ. ID NO:24 | 3 |
| Y0241-4 | QQYSAVPWT | SEQ. ID NO:25 | 4 |
| Y0241-5 | QQYSSVPWT | SEQ. ID NO:26 | 1 |

TABLE 8

Protein sequences of anti-VEGF variants from library YC-95
Round 5 (VEGF eluted phage)

| Name | VH3 sequence (residues 99–111) + insertions | SEQ ID NO: | (# clones/10) |
|---|---|---|---|
| Y0228-1 | YPHYYAKERSSHWYPDV | SEQ. ID NO:27 | 1 |
| Y0228-2 | YPHYYVGETSSHWYPDV | SEQ. ID NO:28 | 1 |
| Y0228-3 | YPHYYARDRSSHWYPDV | SEQ. ID NO:29 | 1 |
| Y0228-4 | YPHYYERDGKSSHWYPDV | SEQ. ID NO:30 | 1 |
| Y0228-5 | YPHYYRNEKSSHWYPDV | SEQ. ID NO:31 | 1 |
| Y0228-6 | YPHYYVGEQSSHWYFDV | SEQ. ID NO:32 | 1 |
| Y0228-7 | YPHYYQRDRSSHWYPDV | SEQ. ID NO:33 | 1 |
| Y0228-8 | YPHYYQKQSKSSHWYFDV | SEQ. ID NO:34 | 1 |
| Y0228-9 | YPHYYQNEGPSSHWYPDV | SEQ. ID NO:35 | 1 |
| Y0228-10 | YPHYYGNHRSSHWYFDV | SEQ. ID NO:36 | 1 |

TABLE 9

Protein sequences of anti-VEGF variants from library YC-95 Round 5 (HCl eluted phage)

| Name | VH3 sequence (residues 99–111) + insertions | SEQ ID NO: | (# clones/10) |
|---|---|---|---|
| Y0229-1 | YPHYYRTEKSSHWYFDV | SEQ. ID NO:37 | 1 |
| Y0229-2 | YPHYYLKDRSSHWYFDV | SEQ. ID NO:38 | 1 |
| Y0229-4 | YPHYYQDEKSSHWYFDV | SEQ. ID NO:39 | 1 |
| Y0229-5 | YPHYYVGEKSSHWYFDV | SEQ. ID NO:40 | 1 |
| Y0229-6 | YPHYYRDERSSHWYFDV | SEQ. ID NO:41 | 1 |
| Y0229-7 | YPHYYTYDKSSHWYFDV | SEQ. ID NO:42 | 1 |
| Y0229-8 | YPHYYHTRGGSSHWYFDV | SEQ. ID NO:43 | 1 |
| Y0229-9 | YPHYYLNDKSSHWYFDV | SEQ. ID NO:44 | 1 |
| Y0229-10 | YPHYYYRDRSSHWYFDV | SEQ. ID NO:45 | 1 |
| *Y0239-1 | | | 1 |

TABLE 10

Protein sequences of anti-VEGF variants from library YC-95 Round 7 (HCl eluted phage)

| Name | VH3 sequence (residues 99–111) + insertions | SEQ ID NO: | (# clones/10) |
|---|---|---|---|
| Y0239-1 | YPHYYRNERSSHWYFDV | SEQ. ID NO:46 | 1 |
| Y0239-2 | YPHYYKNDKSSHWYFDV | SEQ. ID NO:47 | 1 |
| Y0239-3 | YPHYYLADRSSHWYFDV | SEQ. ID NO:48 | 1 |
| Y0239-4 | YPRYYNNERSSHWYFDV | SEQ. ID NO:49 | 1 |
| Y0239-5 | YPHYYLKDKSSHWYFDV | SEQ. ID NO:50 | 1 |
| Y0239-6 | YPHYYLKDGRSSHWYFDV | SEQ. ID NO:51 | 1 |
| Y0239-7 | YPHYYERDGRSSHWYFDV | SEQ. ID NO:52 | 1 |
| Y0239-8 | YPHYYLRDGRSSHWYFDV | SEQ. ID NO:53 | 1 |
| Y0239-9 | YPHYYLGESSHWYFDV | SEQ. ID NO:54 | 1 |
| Y0239-10 | YFHYYLGEKSSHWYFDV | SEQ. ID NO:55 | 1 |

TABLE 11

Protein sequences of anti-VEGF variants from library YC-95 Round 8 (HCl eluted phage)

| Name | VH3 sequence (residues 99–111) + insertions | SEQ ID NO: | (# clones/10) |
|---|---|---|---|
| Y0261-1 | YPHYYLKDRRSSHWYFDV | SEQ. ID NO:56 | 2 |
| Y0261-2 | YPHYYLKDGMSSHWYFDV | SEQ. ID NO:57 | 2 |
| *Y0239-4 | | | 1 |
| *Y0239-9 | | | 5 |

TABLE 12

Protein sequences of anti-VEGF variants from library YC-98 Round 5 (VEGF eluted phage)

| Name | VH3 sequence (residues 99–111) + insertions | SEQ ID NO: | (# clones/10) |
|---|---|---|---|
| Y0228-11 | YPHYYEKQRSHWYFDV | SEQ. ID NO:58 | 1 |
| Y0228-12 | YPHYYKEDKKSHWYFDV | SEQ. ID NO:59 | 1 |
| Y0228-13 | YPHYYSHQKRSHWYFDV | SEQ. ID NO:60 | 1 |
| Y0228-14 | YPHYYSGERESHWYFDV | SEQ. ID NO:61 | 1 |
| Y0228-15 | YPHYYQSEGRSHWYFDV | SEQ. ID NO:62 | 1 |
| Y0228-16 | YPHYYSVEGGSHWYFDV | SEQ. ID NO:63 | 1 |
| Y0228-17 | YPHYYPSPRGSHWYFDV | SEQ. ID NO:64 | 1 |
| Y0228-18 | YPHYYQRNGKSHWYFDV | SEQ. ID NO:65 | 1 |
| Y0228-19 | YPHYYAREGGSHWYFDV | SEQ. ID NO:66 | 1 |
| Y0228-20 | YPHYYSNERKSHWYFDV | SEQ. ID NO:67 | 1 |

TABLE 13

Protein sequences of anti-VEGF variants from library YC-98 Round 5 (HCl eluted phage)

| Name | VH3 sequence (residues 99-111) + insertions | SEQ ID NO: | (# clones/10) |
|---|---|---|---|
| Y0229-11 | YPHYYRGDRKSHWYFDV | SEQ. ID NO:68 | 1 |
| Y0229-12 | YPHYYSDEKKSHWYFDV | SEQ. ID NO:69 | 1 |
| Y0229-13 | YPHYYRSQRKSHWYFDV | SEQ. ID NO:70 | 1 |
| Y0229-14 | YPHYYAWRDRRSHWYFDV | SEQ. ID NO:71 | 1 |
| Y0229-15 | YPHYYANRERKSHWYFDV | SEQ. ID NO:72 | 1 |
| Y0229-16 | YPHYYVNDKTSHWYFDV | SEQ. ID NO:73 | 1 |
| Y0229-17 | YPHYYVEETESHWYFDV | SEQ. ID NO:74 | 1 |
| Y0229-18 | YPHYYEKERKSHWYFDV | SEQ. ID NO:75 | 1 |
| Y0229-19 | YPHYYSHERVSHWYFDV | SEQ. ID NO:76 | 1 |

TABLE 14

Protein sequences of anti-VEGF variants from library YC-98 Round 7 (HCl eluted phage)

| Name | VH3 sequence (residues 99-111) + insertions | SEQ ID NO: | (# clones/10) |
|---|---|---|---|
| Y0239-11 | YPHYYRDERESHWYFDV | SEQ. ID NO:77 | 1 |
| Y0239-12 | YPHYYAHEKKSHWYFDV | SEQ. ID NO:78 | 1 |

TABLE 14-continued

Protein sequences of anti-VEGF variants from library YC-98
Round 7 (HCl eluted phage)

| Name | VH3 sequence (residues 99-111) + insertions | SEQ ID NO: | (# clones/10) |
|---|---|---|---|
| Y0239-13 | YPHYYLKDRKSHWYFDV | SEQ. ID NO:79 | 1 |
| YC239-14 | YPHYYQHDRTSHWYFDV | SEQ. ID NO:80 | 1 |
| Y0239-15 | YPHYYVTDRKSHWYFDV | SEQ. ID NO:81 | 1 |
| Y0239-16 | YPHYYLRDKKSHWYFDV | SEQ. ID NO:82 | 1 |
| Y0239-17 | YPHYYSHERKSHWYFDV | SEQ. ID NO:83 | 1 |
| Y0239-18 | YPHYYLNERKSHWYFDV | SEQ. ID NO:84 | 1 |
| Y0239-19 | YPHYYVNERKSHWYFDV | SEQ. ID NO:85 | 2 |
| Y0240-1 | YPHYYLTDHKSHWYFDV | SEQ. ID NO:86 | 1 |

TABLE 15

Protein sequences of anti-VEGF variants from library YC-98
Round 8 (HCl eluted phage)

| Name | VH3 sequence (residues 99-111) + insertions | SEQ ID NO: | (# clones/10) |
|---|---|---|---|
| Y0261-4 | YPHYYLKDGKKSHWYFDV | SEQ. ID NO:87 | 1 |
| Y0261-5 | YPHYYRRDKKSHWYFDV | SEQ. ID NO:88 | 1 |
| Y0261-6 | YPHYYLKDKKSHWYFDV | SEQ. ID NO:89 | 1 |
| Y0261-7 | YPHYYLHDRKSHWYFDV | SEQ. ID NO:90 | 1 |
| Y0261-8 | YPHYYLSDKKSHWYFDV | SEQ. ID NO:91 | 1 |
| Y0239-19 | YPHYYVNERKSHWYFDV | SEQ. ID NO:92 | 1 |
| *Y0239-13 | | | |
| *Y0239-16 | | | |

In order to quantify relative antigen-binding affinities, several anti-VEGF variants' DNA were transformed into *E. coli* strain 34B8, expressed as Fab, and purified by passing the periplasmic shockate through a protein G column (Pharmacia) as described in WO98/45331.

CDR combination Variant Y0313-2: An attempt was made to improve antigen binding affinity by combining a previously discovered CDR VH2 mutation with an insertion variant described here. A mutagenic oligonucleotide, YC-107 (Table 16) was used to combine insertion mutations found in CDR VH3, from clone Y0239-19, with VH2 CDR mutations T28D/N31H from clone Y0243-1 (WO98/45331) of CDR VH2.

TABLE 16

Mutagenesis oligo for adding a CDR insertion peptide

| Oligo # | Region | (Comments) | Sequence | SEQ. ID NO: |
|---|---|---|---|---|
| YC-107 | VH3 | (insert VNERK from library YC-98) | TAC CCG CAC TAT TAT GTG AAC GAG CGG AAG AGC CAC TGG TAT TTC | SEQ. ID NO:93 |

The resulting combined CDR variant was designated Y0313-2. A Fab protein sample was prepared as described above for BIACORE™ analysis.

BIACORE™ Analysis: The VEGF-binding affinities of Fab fragments were calculated from association and dissociation rate constants measured using a BIACORE™-2000 surface plasmon resonance system (BIACORE™, Inc., Piscataway, N.J.). A biosensor chip was activated for covalent coupling of VEGF using N-ethyl-N'-(3-dimethylaminopropyl)-carbodiimide hydrochloride (EDC) and N-hydroxysuccinimide (NHS) according to the supplier's (BIACORE™, Inc., Piscataway, N.J.) instructions. VEGF(8-109) was buffered exchanged into 20 mM sodium acetate, pH 4.8 and diluted to approximately 50 μg/mL. Aliquots of VEGF were injected at a flow rate of 2 μL/min to achieve approximately 700–1400 response units (RU) of coupled protein. A solution of 1 M ethanolamine was injected as a blocking agent.

For kinetics measurements, two-fold serial dilutions of Fab were injected in PBS/TWEEN buffer (0.05% TWEEN 20™ in phosphate buffered saline) at 25° C. at a flow rate of 10 μL/min. Equilibrium dissociation constants, Kd's from SPR measurements were calculated as koff/kon (Table 17).

TABLE 17

Kinetics of Fab-VEGF binding from BIACORE™ measurements.

| Variant | Kon ($10^4$/M/s) | koff ($10^{-4}$/s) | Kd (nM) | Kd (wt)/Kd (mut) |
|---|---|---|---|---|
| Y0192 | 4.1 | 1.21 | 2.9 | 1 |
| Y0241-4 | 4.4 | 1.41 | 3.2 | 0.9 |
| Y0241-7 | 4.6 | 1.28 | 3.0 | 1.0 |
| Y0241-6 | 4.7 | 1.29 | 2.7 | 1.1 |

TABLE 17-continued

Kinetics of Fab-VEGF binding from BIACORE ™ measurements.

| Variant | Kon ($10^4$/M/s) | koff ($10^{-4}$/s) | Kd (nM) | Kd (wt)/Kd (mut) |
|---|---|---|---|---|
| Y0242-1 | 4.7 | 0.86 | 1.8 | 1.6 |
| Y0239-19 | 3.6 | 0.10 | 0.30 | 9.7 |
| Y0239-8 | 3.8 | 0.18 | 0.50 | 5.8 |
| Y0240-1 | 2.5 | 0.13 | 0.50 | 5.8 |
| Y0239-2 | 3.6 | 1.64 | 4.6 | 0.6 |
| Y0239-12 | 5.7 | 0.34 | 0.6 | 4.8 |
| Y0239-9 | 3.97 | 0.19 | 0.5 | 6.0 |
| Y0261-6 | 4.4 | 0.25 | 0.6 | 5.0 |
| Y0313-2 | 3.11 | 0.11 | 0.36 | 8.0 |

Results of SPR measurements demonstrated that affinity is mainly enhanced through a slower dissociation rate (as opposed to faster association).

For the insertion variant Y0239-19, an approximately 10-fold improvement in binding affinity was observed (Table 17). However, addition of the VH1 mutations did not further improve affinity, as indicated for the variant Y0313-2.

Cell-Based Assay of VEGF: Two Fab variants of the anti-VEGF antibody were tested for their ability to antagonize VEGF (recombinant; version 1–165) in induction of the growth of HuVECs (human umbilical vein endothelial cells). The alamar blue assay (H. Gazzano-Santoro, et al. *J Immunol Methods* 202:163–171 (1997)) was used to measure the metabolic activity of cells in response to VEGF.

Two Fab variants of the anti-VEGF antibody were tested for their ability to antagonize VEGF (recombinant; version 1–165) activity in induction of the growth of HuVECs (human umbilical vein endothelial cells). HuVEC cells are seeded (1500/well) in a 96 well microtiter plate in complete medium (Cell Systems, Kirkland, Wash.) that has been coated with Cell Systems attachment factor. The cells are allowed to attach for 24 hrs. On day 2, VEGF and Fab are diluted in assay medium (DMEM/F12 +pennicillin/streptomycin, 0.1% gelatin). For the antibody experiments, a constant concentration of 5 ng/ml VEGF is added to all the wells followed by the addition of various concentrations of anti-VEGF Fab (approximately 10 µg/ml and dilutions). The VEGF and Fab incubate with the HUVEC cells for 2 days, after which 25 µl of alamar blue is added. Following a 4 hr incubation period, fluorescence is read on a Cytoflour Fluorescence Plate reader. The media used for these assays is from Cell Systems.

The results (FIG. 2) show that the insertion variant Y0313-2 Fab has roughly 100-fold enhanced potency over the original humanized antibody, F(ab)-12.

Crystallization and X-Ray Structure Determination of the Insert-Fab Y0313-2 in complex with VEGF: Crystals of VEGF in complex with the Fab fragment Y0313-2 were grown at room temperature by vapor diffusion using the hanging drop method. Crystallization buffer containing 0.1 M sodium chloride, 20 mM Tris at pH 7.5, and the VEGF:Fab complex at a concentration of 8 mg/ml was mixed with an equal amount of reservoir solution (15% PEG 4000, 5% isopropanol, 0.1M MES, pH 6.0, 0.2 M Citrate, 0.2 M Ammonium sulfate and 1 mM SPADNS (2-(p-sulfophenylazo)-1,8-dihydroxy-3,6-naphthalene disulphonic acid)). The resulting crystals belong to the monoclinic space group P2 with cell parameters of a=107.6 Å, b=65.8 Å, c=123.8 Å, and β=93.4° and contain one VEGF-dimer bound to two Fab fragments in the asymmetric unit.

Prior to flash cooling with liquid nitrogen, crystals were dipped into artificial mother liquor containing 20% glycerol. One diffraction data set was collected from a single crystal at 100 K on a CCD detector at the Advanced Light Source (Berkeley, Calif.). The data were processed using MOSFLM (Leslie, A MOSFLM Users Guide, MRC-LMB, Cambridge (1994)) and programs of the CCP4 suite (Collaborative Computing Project No. 4 Acta Crystallog. sect. D, 50: 760–763 (1994)). The final data set was of good quality (Rsym=7.4%) with a completeness of 94.5% for all reflections between 25 Å and 2.8 Å resolution.

Initial phases for the complex were obtained by molecular replacement, using the constant domains and the variable domains of the Fab fragment F(ab)-12 as separate search models. A model of the receptor binding domain of VEGF could be placed unambiguously in a resulting difference density map.

Refinement of the model with program X-PLOR (Bruenger et al. Science 235: 458–460. (1987)) resulted in a final R-value of 21.2% with an R-free of 26.6% using all data between 2.8 Å and 25 Å.

New Antibody-Antigen Contacts in the Insert-Fab Complex with VEGF: The results of x-ray crystallography show that the introduction of the insert (Asn 104a, Glu 104b and Arg 104c (note: numbering of Y0313-2 residues is sequential with inserted residues given a letter, rather than according to Kabat et al., supra) together with the two substitutions (G104V and S105K) enclosing it, increases the total amount of buried surface in the interface between VEGF and the antibody by about 20% (see FIG. 4), as compared with the structure of the F(ab)-12 complex (Muller et al., Structure 6(9):1153–1167 (1998)). The main contributors for the enlargement of the contact area are residues Val 104 and Arg 104c. Together, these two residues account for additional 220 Å$^2$ of buried surface on the Fab fragment. The side chain of Val 104 is packing tightly against the main chain of residues 93 to 95 of VEGF. The newly introduced Arg 104c forms a charged interaction with the carboxyl group of Asp 41 of VEGF and is also in contact with the phenyl ring of Tyr 39 (see FIG. 5). Minor contributions to the interface are made by the side chain of Lys 105 which is in the vicinity of the VEGF residues Glu 44 and Tyr 45. The side chains of residues Asn 104a and Glu 104b are pointing away from the interface and neither of them contributes significantly to the interface between the Fab fragment and VEGF.

What is claimed is:

1. A heavy chain variable domain of an antibody that binds vascular endothelial growth factor (VEGF) comprising the amino acid sequence of SEQ ID NO:98 or SEQ ID NO:99.

2. An antibody variant that binds vascular endothelial growth factor (VEGF) and comprises the heavy and light chain variable domains of Y0239-19 (SEQ ID NOS: 98 and 95, respectively).

3. An antibody variant that binds vascular endothelial growth factor (VEGF) and comprises the heavy and light chain variable domains of Y0313-2 (SEQ ID NOS: 99 and 95, respectively).

* * * * *